(12) United States Patent  
Waxman et al.

(10) Patent No.: US 11,143,572 B2  
(45) Date of Patent: **\*Oct. 12, 2021**

(54) HYDROCARBON LEAK IMAGING AND QUANTIFICATION SENSOR

(71) Applicant: MultiSensor Scientific, Inc., Cambridge, MA (US)

(72) Inventors: Allen M. Waxman, Newton, MA (US); Jason M. Bylsma, Boston, MA (US); Allan Vaitses, Marion, MA (US)

(73) Assignee: MultiSensor Scientific, Inc., Cambridge, MA (US)

( \* ) Notice: Subject to any disclaimer, the term of this patent is extended or adjusted under 35 U.S.C. 154(b) by 439 days.

This patent is subject to a terminal disclaimer.

(21) Appl. No.: 16/183,072

(22) Filed: Nov. 7, 2018

(65) Prior Publication Data

US 2019/0195725 A1 Jun. 27, 2019

Related U.S. Application Data

(63) Continuation of application No. 15/598,052, filed on May 17, 2017, now Pat. No. 10,197,470.

(Continued)

(51) Int. Cl.
*G01M 3/38* (2006.01)
*G01N 21/3504* (2014.01)
(Continued)

(52) U.S. Cl.
CPC .............. *G01M 3/38* (2013.01); *G01N 21/31* (2013.01); *G01N 21/3504* (2013.01);
(Continued)

(58) Field of Classification Search
CPC ......... G01M 3/38; G01N 21/85; G01N 21/31; G01N 21/3103; G01N 21/35;
(Continued)

(56) References Cited

U.S. PATENT DOCUMENTS 3,517,190 A 6/1970 Astheimer
3,662,171 A 5/1972 Brengman et al.
(Continued)

FOREIGN PATENT DOCUMENTS

CN 1479866 A 3/2004
CN 1888865 A 1/2007
(Continued)

OTHER PUBLICATIONS

International Search Report, International Application No. PCT/US2018/050760 (Systems and Methods for Multispectral Imaging and Gas Detection Using a Scanning Illuminator and Optical Sensor, filed Sep. 12, 2018), issued by ISA/European Patent Office, 7 pages, dated Mar. 8, 2019.
(Continued)

*Primary Examiner* — Nathaniel J Kolb
(74) *Attorney, Agent, or Firm* — Choate, Hall & Stewart LLP; William R. Haulbrook; Ronen Adato

(57) ABSTRACT

This invention consists of sensors and algorithms to image, detect, and quantify the presence of hydrocarbon gas (for example from leaks) using a short-wave infrared radiation detector array with multiple spectral filters under natural sunlight or artificial illumination, in combination with the hydrodynamics of turbulent gas jets and buoyant plumes. Multiple embodiments are recited and address detection and quantification of methane gas leaks. Quantification includes gas column densities, gas concentration estimates, total mass, hole size estimates, and estimated emission flux (leak rate) of gas from holes and cracks in pressurized vessels, pipes, components, and general gas infrastructure, and from surface patches (for example due to gas leaks in underground pipes) under the action of buoyancy and wind. These and similar embodiments are applicable more generally to natural gas and other hydrocarbon gases, liquids, emulsions, (Continued)

solids, and particulates, and to emissions monitoring of greenhouse gases methane and carbon dioxide.

27 Claims, 15 Drawing Sheets
(6 of 15 Drawing Sheet(s) Filed in Color)

Related U.S. Application Data

(60) Provisional application No. 62/472,463, filed on Mar. 16, 2017, provisional application No. 62/338,255, filed on May 18, 2016.

(51) Int. Cl.
| | |
|---|---|
| *G01N 21/359* | (2014.01) |
| *G01N 21/31* | (2006.01) |
| *G01N 21/85* | (2006.01) |
| *G01N 33/00* | (2006.01) |
| *G01J 3/28* | (2006.01) |
| *G01F 1/66* | (2006.01) |

(52) U.S. Cl.
CPC ........... *G01N 21/359* (2013.01); *G01N 21/85* (2013.01); *G01N 33/0036* (2013.01); *G01F 1/661* (2013.01); *G01J 2003/2826* (2013.01); *G01N 2021/3513* (2013.01); *G01N 2021/3531* (2013.01); *G01N 2021/8578* (2013.01); *Y02A 50/20* (2018.01)

(58) Field of Classification Search
CPC ........... G01N 21/3504; G01N 21/2021; G01N 21/8578; G01N 21/3129; G01N 21/3188
USPC ................. 73/40, 40.5 R, 49.1–49.3
See application file for complete search history.

(56) References Cited

U.S. PATENT DOCUMENTS

| | | | |
|---|---|---|---|
| 4,264,209 A | 4/1981 | Brewster | |
| 4,490,613 A | 12/1984 | Brame | |
| 4,543,481 A * | 9/1985 | Zwick | G01M 3/38 250/338.5 |
| 4,555,627 A | 11/1985 | McRae, Jr. | |
| 4,864,127 A | 9/1989 | Brame | |
| 4,999,498 A | 3/1991 | Hunt et al. | |
| 5,103,675 A | 4/1992 | Komninos | |
| 5,281,816 A | 1/1994 | Jacobson et al. | |
| 5,306,913 A | 4/1994 | Noack et al. | |
| 5,656,813 A | 8/1997 | Moore et al. | |
| 6,061,141 A | 5/2000 | Goldenberg et al. | |
| 6,680,778 B2 | 1/2004 | Hinnrichs et al. | |
| 6,690,472 B2 | 2/2004 | Kulp et al. | |
| 7,075,653 B1 | 7/2006 | Rutherford | |
| 7,486,399 B1 | 2/2009 | Reichardt et al. | |
| 7,649,174 B2 | 1/2010 | Mammen et al. | |
| 7,977,639 B2 | 7/2011 | Maillart et al. | |
| 8,193,496 B2 | 6/2012 | Furry | |
| 8,426,813 B2 | 4/2013 | Furry | |
| 8,730,477 B2 | 5/2014 | Ruhland et al. | |
| 9,228,938 B2 | 1/2016 | Hager et al. | |
| 9,955,910 B2 | 5/2018 | Fright et al. | |
| 10,031,040 B1 | 7/2018 | Smith et al. | |
| 10,190,976 B2 | 1/2019 | Waxman et al. | |
| 10,197,470 B2 * | 2/2019 | Waxman | G01N 21/31 |
| 10,330,593 B1 | 6/2019 | Dobler et al. | |
| 10,371,627 B2 | 8/2019 | Waxman et al. | |
| 10,436,710 B2 | 10/2019 | Waxman et al. | |
| 10,921,243 B2 | 2/2021 | Waxman et al. | |
| 10,976,245 B2 | 4/2021 | Waxman et al. | |
| 2002/0071122 A1 | 6/2002 | Kulp et al. | |
| 2004/0051043 A1 | 3/2004 | Kilian et al. | |
| 2006/0202122 A1 | 9/2006 | Gunn et al. | |
| 2006/0203248 A1 | 9/2006 | Reichardt et al. | |
| 2008/0069177 A1 | 3/2008 | Minor et al. | |
| 2010/0127173 A1 | 5/2010 | Schmidt | |
| 2010/0231722 A1 | 9/2010 | Hill, Jr. et al. | |
| 2010/0241361 A1 | 9/2010 | Hofvander et al. | |
| 2012/0062697 A1 | 3/2012 | Treado et al. | |
| 2012/0062740 A1 | 3/2012 | Treado et al. | |
| 2013/0327942 A1 | 12/2013 | Silny | |
| 2014/0002667 A1 | 1/2014 | Cheben et al. | |
| 2014/0008526 A1 | 1/2014 | Zeng et al. | |
| 2014/0104607 A1 | 4/2014 | Treado et al. | |
| 2014/0118722 A1 | 5/2014 | Treado et al. | |
| 2014/0160479 A1 * | 6/2014 | Hager | G01N 21/3504 356/438 |
| 2014/0268104 A1 | 9/2014 | Treado et al. | |
| 2015/0069239 A1 | 3/2015 | Kester et al. | |
| 2015/0316473 A1 * | 11/2015 | Kester | G01J 3/2803 250/339.02 |
| 2015/0323449 A1 * | 11/2015 | Jones | G01M 3/38 356/437 |
| 2016/0069743 A1 | 3/2016 | McQuilkin et al. | |
| 2016/0097713 A1 | 4/2016 | Kester et al. | |
| 2016/0131576 A1 | 5/2016 | Cabib et al. | |
| 2016/0334538 A1 | 11/2016 | Rieker et al. | |
| 2016/0345835 A1 | 12/2016 | Darty | |
| 2016/0349228 A1 * | 12/2016 | Kester | G01J 3/36 |
| 2017/0234761 A1 | 8/2017 | Augusto | |
| 2017/0284891 A1 | 10/2017 | Miranda | |
| 2017/0336281 A1 | 11/2017 | Waxman et al. | |
| 2017/0336320 A1 | 11/2017 | Yalin | |
| 2018/0045596 A1 | 2/2018 | Prasad et al. | |
| 2018/0231684 A1 * | 8/2018 | Jones | G01N 21/552 |
| 2018/0266944 A1 | 9/2018 | Waxman et al. | |
| 2019/0137390 A1 | 5/2019 | Waxman et al. | |
| 2019/0145891 A1 | 5/2019 | Waxman et al. | |
| 2019/0170900 A1 | 6/2019 | Rieker et al. | |
| 2019/0277753 A1 | 9/2019 | Waxman et al. | |
| 2020/0240906 A1 | 7/2020 | Waxman et al. | |

FOREIGN PATENT DOCUMENTS

| | | | |
|---|---|---|---|
| CN | 101529219 A | 9/2009 | |
| CN | 101680833 A | 3/2010 | |
| CN | 101696897 A | 4/2010 | |
| CN | 103503135 A | 1/2014 | |
| CN | 104101571 A | 10/2014 | |
| CN | 104122039 A | 10/2014 | |
| CN | 104697718 A | 6/2015 | |
| CN | 205049297 U | 2/2016 | |
| CN | 205562132 U | 9/2016 | |
| CN | 106124130 A | 11/2016 | |
| JP | H05264446 A | 10/1993 | |
| WO | WO-02/27297 A1 | 4/2002 | |
| WO | WO-2017/201194 A1 | 11/2017 | |
| WO | WO-2018/170438 A1 | 9/2018 | |
| WO | WO-2019/099096 A1 | 5/2019 | |
| WO | WO-2020/154619 A2 | 7/2020 | |

OTHER PUBLICATIONS

Written Opinion, International Application No. PCT/US2018/050760 (Systems and Methods for Multispectral Imaging and Gas Detection Using a Scanning Illuminator and Optical Sensor, filed Sep. 12, 2018), issued by ISA/European Patent Office, 12 pages, dated Mar. 8, 2019.
Benson, R. et al., Standoff passive optical leak detection of volatile organic compounds using a cooled InSb based infrared imager, Proceedings of the Air & Waste Management Assoc. Conf. Extended Abstract No. 06-A-131-AQMA, pp. 1-10 (2006).
Buchwitz, M. et al., Atmosphere methane and carbon dioxide from SCIAMACHY satellite data, Atmos. Chem. Phys., 5:941-962 (2005).
Byer, R. L. and Shepp, L. A., Two-dimensional remote air-pollution monitoring via tomography, Optics Letters, 4(3):75-77 (1979).
Clark, R. N. et al., Reflectance spectroscopy of organic compounds: Alkanes, J. Geophysical Research, 114:E030001:1-19, (2009).
Epperson, D. et al., Equivalent Leak Definitions for Smart LDAR

(56) References Cited

OTHER PUBLICATIONS (Leak Detection and Repair) When Using Optical Imaging Technology, Journal of the Air & Waste Management Association, 57(9):1050-1060, (2007).

Furry, D. et al., Detection of Volatile Organic Compounds (VOC's) with a Spectrally Filtered Cooled Mid-Wave Infrared Camera, Inframation Proceedings, Document No. ITC 108A 2005-06-01, 6 pages, (2005).

Gottwald, M. et al., The Instrument, Chapter 3 in SCHIAMACHY—Exploring the Changing Earth's Atmosphere, pp. 29-46, (2006).

Gross, W. et al., Localization of Methane Distributions by Spectrally Tuned Infrared Imaging, SPIE, Part of the SPIE Conference on Air Monitoring and Detection of Chemical and Biological Agents, 3533:234-240, (1998).

Inada, H. et al., Uncooled SWIR InGaAs/GaAsSb type II quantum wells focal plane array, Proc. of SPIE, Infrared Technology and Applications XXXVI, 7660:76603N-1-76603N-7 (2010).

International Search Report and Written Opinion, International Application No. PCT/US2017/033157 (Hydrocarbon Leak Imaging and Quantification Sensor, filed May 17, 2017), issued by ISA/US, Commissioner for Patents, 12 pages, dated Sep. 14, 2017.

International Search Report, International Application No. PCT/US18/22943 (Scanning IR Sensor for Gas Safety and Emissions Monitoring, filed Mar. 16, 2018), issued by ISA/US, Commissioner for Patents, 4 pages, dated Aug. 8, 2018.

Shulz, M. et al., High-resolution thermophysical measurements using staring infrared detector arrays, High Temperatures—High Pressures, 32:547-556 (2000).

Van Den Bosch, C. J. H. and Duijm, N. J., Overflow and Spray release, Chapter 2, Methods for Calculation of Physical Effects: Due to Release of Hazardous Materials (Liquids & Gases)., EDS: Van den Bosch et al., 3rd Ed. 2nd Printing, CPR 14E, TNO—The Netherlands Organization of Applied Scientific Research, p. 2.1-2.179 (2005).

Written Opinion, International Application No. PCT/US18/22943 (Scanning IR Sensor for Gas Safety and Emissions Monitoring, filed Mar. 16, 2018), issued by ISA/US, Commissioner for Patents, 9 pages, dated Aug. 8, 2018.

Li, Jing, et al. Remote Sensing System of Natural Gas Leakage Based on Multiple Characteristic Wavelength Spectral Analysis, Spectroscopy and Spectral Analysis, English Abstract and Machine Translation included, 34(5):1249-1252, (2014).

Zhaoci, L. et al., LNG continuous leakage and diffusion process simulation, CIESC Journal, 66(S2):158-165, (2015).

\* cited by examiner

Examples of Gas Leak Imaging
Natural Gas Plume from 10mm
Orifice at 1/4 psig in Mild Wind
Methane Jet from a Loose Hammer
Union at 500 psig in 9kph Wind
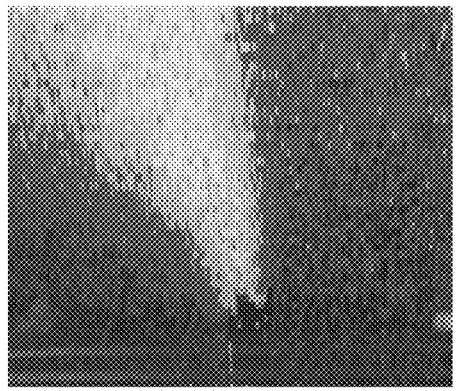
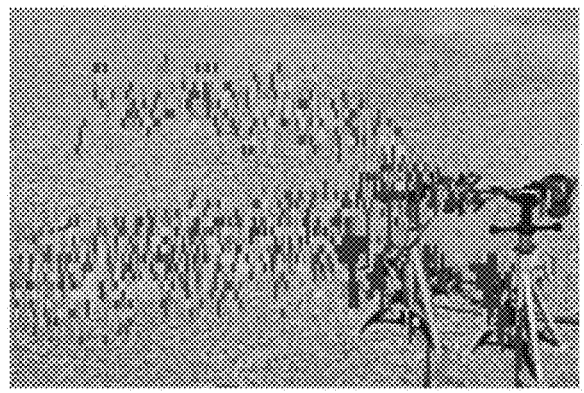
FIG. 4A
FIG. 4B
Surface Emissions from an Underground
Gas Pipe Leak on a Boston Area Street
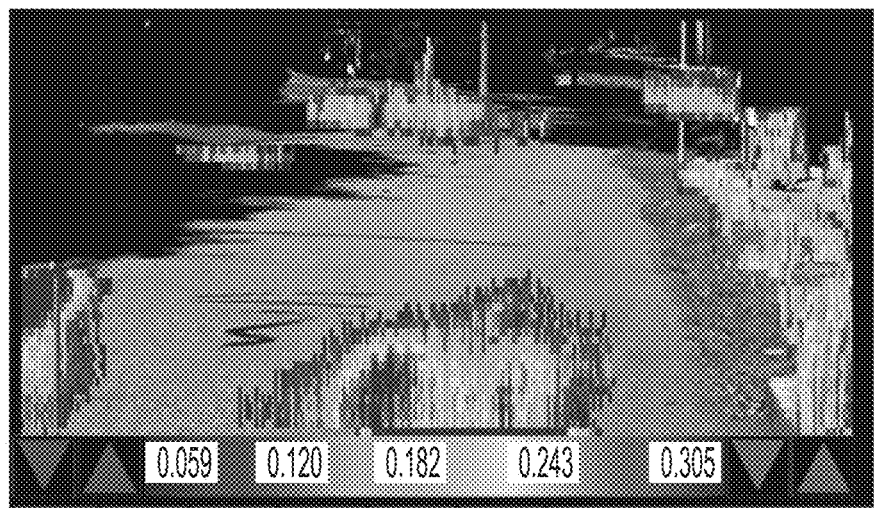
FIG. 4C Methane Surface Patch Imaging Geometry (Side View)

Methane Surface Patch Emission Geometry (Plan View)

HYDROCARBON LEAK IMAGING AND QUANTIFICATION SENSOR

CROSS-REFERENCE TO RELATED APPLICATIONS

This application is a continuation of U.S. patent application Ser. No. 15/598,052, filed May 16, 2017 (now U.S. Pat. No. 10,197,470, issued Feb. 5, 2018), which claims priority from provisional patent applications U.S. 62/338,255 filed May 18, 2016 and U.S. 62/472,463, filed Mar. 16, 2017 both by the present inventors.

FEDERALLY SPONSORED RESEARCH

None

SEQUENCE LISTING

None

TECHNICAL FIELD OF INVENTION

This invention refers generally to optical detection and quantification of natural gas and other hydrocarbon gas leaks, from holes and cracks in pressurized vessels, pipes, components, and general gas infrastructure, and from emissions emanating from surfaces due to gas leaks in underground gas infrastructure or naturally occurring surface emissions. It may also be useful in assessing methane emissions from livestock.

BACKGROUND—PRIOR ART

Landau, L. D., & Lifshitz, E. M., "Fluid Mechanics", Pergamon Press (1959).
Abramovich, G. N., "The Theory of Turbulent Jets", MIT Press (1966).
Thomas, G. E., & Stamnes, K., "Radiative Transfer in the Atmosphere and Ocean", Cambridge University Press (1999).
Lee, J. H. W., & Chu, V. H., "Turbulent Jets and Plumes: A Lagrangian Approach", Kluwer Academic Publishers (2003).
Green, D. W., & Perry, R. H., "Perry's Chemical Engineers' Handbook," $8^{th}$ Ed., McGraw-Hill Publishers (2007).

BACKGROUND ART

Natural gas leaks create both safety and environmental hazards, and occur along the entire gas supply chain from the well to the street (so-called upstream, midstream, and downstream sectors). Methane, the primary constituent of natural gas is combustible in air, and is also a potent greenhouse gas. Other hydrocarbons found in natural gas, as well vapors emanating from liquids separated from gas and oil include ethane, propane, butane, pentane, hexane, octane, and heavier hydrocarbons, which form volatile organic compounds that generate smog which is a health hazard. Thus, there are compelling reasons to detect leaks of methane gas and other hydrocarbon gases, so that such leaks can be repaired. However, in order to repair such leaks, it is necessary to also localize the leak, and in order to prioritize repairs it is desirable to quantify the leak in terms of leak rate or emission flux. Estimating gas emission flux is also needed to assess environmental impact of greenhouse gases. Moreover, it is desirable to have a means to monitor or inspect wide areas for such leaks and do so quickly from a safe and practical standoff distance, while maintaining the ability to pinpoint the leak location and estimate the leak rate. It is also desirable to conduct effective leak monitoring in the presence of naturally occurring ambient gases and vapors, such as water vapor, and regardless of the relative temperature between leaked gas and the background environment. A cost-effective solution is also necessary if such solutions are to be broadly adopted and utilized.

Gas detectors can be classified according to their coverage extent, as either spot sensors, line sensors or area sensors. Spot sensors, often referred to as sniffers, draw in a local sample of air and detect the presence of a combustible or toxic gas by means of various analytical methods. They can be fixed in place for continuous monitoring, or hand portable for inspections, but they require direct sampling in place and provide very limited coverage. They may provide concentration measurements, but do not provide leak rate estimates. Other instrumentation is available to locally sample (as opposed to image) known leaks in order to provide an estimate of leak rate, but they too provide only local coverage and require direct collection of gas from the leaking component.

Optical line sensors, also known as open-path gas detectors, employ optical means to detect gas that lies along the line between a dedicated light emitter (e.g., laser, tunable laser, or narrowly focused broadband source) and a dedicated photo-detector (or multiple photo-detectors). Such detectors exploit the absorption of light (typically in different parts of the infrared spectrum) at select wavelengths characteristic of the molecular composition of the gas of interest. These sensors detect gas present anywhere along the line between the light emitter and the photo-detector (or between combined emitter/detector assembly and a remote reflector if the optical path is folded), but they cannot determine where along the path the gas is, nor from where it came, and has limited coverage to only the narrow open path between emitter and detector. By utilizing multiple wavelengths of light, such sensors can measure column density of gas along the open path, but cannot measure or estimate concentration nor leak rate. Open-path sensors can be installed in place, hand portable, or mobile aboard ground and air vehicles. In order to achieve area coverage from a standoff distance, it is recognized that imaging sensors offer many advantages over spot and line sensors, in that they can detect the presence of gas and possibly localize the leak source.

Several gas imaging technologies have been proposed, developed, patented, and are commercially available. They are all based on the absorption of infrared light at wavelengths characteristic of the molecules of interest. For methane and hydrocarbons in general, most imagers operate in select bands of the mid-wave infrared and long-wave infrared spectrum. The leading commercially available gas imaging sensors operate in only a single narrow band of the mid-wave infrared spectrum, and do not provide quantitative data, only pictures to be interpreted by the human operator. Other imaging sensors utilize multiple spectral bands in the long-wave infrared (the so-called "molecular fingerprint region") to detect and discriminate among different hydrocarbon gases, and to quantify the column density of gas at each pixel of the image. Such systems have proven to be both expensive and have significant shortcomings. These mid-wave and long-wave infrared sensors rely on thermally emitted light from the background to illuminate the gas that will absorb at select wavelengths as detected by the imaging sensors. This requires that the background and gas differ in temperature by at least several degrees Celsius, otherwise the light absorbed (or emitted) by the gas will not provide sufficient signal contrast to be reliably detected by the human operators of these thermal sensors. For example, in the case of surface emissions of natural gas due to an underground pipe leak, or methane emissions from a landfill, the gas percolates up through the soil and reaches thermal equilibrium with the soil by the time it emerges from the ground. Thus, there is little or no thermal contrast between the gas and the ground, and so cannot be reliably detected by a thermal infrared sensor. Another major shortcoming of mid-wave and long-wave gas imaging sensors is their poor performance in the presence of water vapor (high humidity, steam), fog and light rain. This is because the spectrum of water overlaps with key spectral features of methane in both the mid-wave and long-wave infrared spectral regions. Thus, water vapor will mask the presence of a methane leak, and conversely, water vapor will trigger a false alarm for methane. As both water vapor and methane are less dense than air, they both rise due to buoyancy and look alike in a spectrally filtered mid-wave or long-wave infrared image. Additionally, all mid-wave infrared and some long-wave infrared gas imaging sensors require cryogenic cooling, which is both expensive and unreliable. It is preferable to utilize only thermo-electric cooling to reduce dark current in gas imaging sensors. Finally, none of the available gas imaging sensors provides a capability to estimate leak rate from a hole, or emission flux from a surface. Some can provide column density of gas at each pixel, and using spatial information of the imaged gas jet, plume or cloud, one can then estimate local or average gas concentration.

In order to overcome the above-cited shortcomings of thermal infrared based imaging sensors for gas detection, it is possible to utilize differential absorption gas imaging in the short-wave infrared part of the spectrum. Atmospheric scientists using satellite-borne sensors like Landsat and SCIAMACHY have exploited this. It enables the detection of methane, other hydrocarbons, carbon dioxide, and other gases in the atmosphere based on molecular absorption of natural sunlight, without confusion of intervening water vapor. Such space-based imaging technologies provide synoptic scale maps of column densities of greenhouse gases and other air pollutants.

It is the purpose of this invention to provide sensors and methods that enable gas leak detection, localization, imaging, and quantification of leak rate or emission mass flux, utilizing multispectral imaging in the short-wave infrared in combination with the hydrodynamics of turbulent gas jets and buoyant plumes. Multiple embodiments of the invention are described and have been developed, that are applicable more generally to natural gas and other hydrocarbon gases, liquids, emulsions, solids, and particulates, and to emissions monitoring of greenhouse gases such as methane and carbon dioxide.

SUMMARY of the INVENTION and its ADVANTAGES

This invention consists of sensors and algorithms for imaging, detection, localization, and quantification of hydrocarbon leaks by means of multispectral sensing using non-thermal infrared radiation from natural sunlight or artificial illumination sources. More specifically, several embodiments of sensor systems are described that incorporate short-wave infrared (SWIR) detector arrays sensitive in the range of approximately 1.0 through 2.6 microns, in combination with two or more spectral filters selected to create Core and Wings spectral bands with respect to a hydrocarbon feature complex in the vicinity of 2.3 microns. Detection is accomplished via absorption spectroscopy using natural sunlight or artificial illumination in direct transmission through a gas to the sensor, or reflected off a background surface with gas located between the background and the sensor. With the system properly calibrated, the resulting multispectral data can be processed in real-time to yield an absorption map or image related to the differential optical depth, or equivalently column density, of an intervening hydrocarbon gas such as methane, the major constituent of natural gas.

The resulting absorption imagery is color mapped to render the degree of gas absorption across the scene, and overlaid on an optically registered color visible image that provides context. In the case of gas leaking from a hole or crack in a pressurized pipe or vessel, the escaping gas forms a turbulent jet or plume that is visible in the absorption image and from which the leak can be localized. The invented methods estimate both the diameter of the effective hole and the mass flux of leaking methane (or other gas) from the data present in this absorption image, if the internal pressure driving the leak is known approximately. In the case of underground gas leaks, such as due to municipal gas infrastructure or gathering lines from gas wells, the gas percolates through the subsurface soil and emerges at the surface, often in disconnected surface patches. These surface emissions diffuse into a thin layer next to the ground and rise (in the case of natural gas) due to buoyancy, but are often blown by ground-level winds. The invented methods estimate both the mass of gas and the mass flux from a surface patch by combining the absorption imagery with wind speed and direction measured near ground level. Flux estimation methods are developed for cases of both steady winds and gusting winds.

Functional prototypes of two embodiments of leak imaging and quantification sensors have been built, and graphical user interfaces to control these sensors and view (and store or transmit) their real-time outputs have been implemented on touch-screen tablet displays. One such embodiment supports video-rate imaging and quantification of gas leaks. A second such embodiment supports scan-based imaging over a programmable and variable wide field-of-regard, trading away video-rate imaging for a lower cost embodiment of an imaging gas sensor. Imagery of gas leaks from holes and surfaces, and leak rate estimates, are shown in the figures to confirm the viability of the invention.

This invention has several key advantages over thermal infrared gas imaging sensors that operate in the mid-wave (MWIR) or long-wave (LWIR) infrared parts of the spectrum. This includes the ability to detect and quantify leaked gas with small or no temperature difference relative to the background, as the invention utilizes SWIR light provided by natural sunlight or by lamps of appropriate color temperature, and does not rely on a thermal contrast between gas and the background or a background of varying temperature. The detectors suitable for use in this invention do not require cryogenic cooling, using instead thermo-electric cooling that is more reliable and less expensive than cryogenic coolers such as a Stirling engine or liquid nitrogen. Finally, the invention can also detect gas leaks in the presence of humidity, steam, fog, and light rain, as the hydrocarbon features detected in the SWIR do not overlap spectral regions where water vapor absorption is significant, which is important as one cannot control the presence of water vapor or fog in the atmosphere between the sensor and the leak source, and many industrial processes purposely mix steam with hydrocarbon gases.

This invention and its various embodiments will be useful in imaging, detecting, localizing, and quantifying natural gas leaks from components along the entire gas supply chain, from the well head to compressors to transmission pipelines to gate stations and underground distribution networks. Detection and quantification of volatile organic compounds (VOCs) in or near refineries, petrochemical plants, hydrocarbon storage tanks, or other industrial and commercial facilities will be possible. Landfill methane emissions mapping will be possible using this invention in combination with tomographic imaging around the periphery of a landfill. Similar tomographic three-dimensional mapping of gas over a refinery is possible, utilizing an airborne variant of this invention. This invention has also been shown to be capable of detecting liquid oil spills on land, sand, seawater, and sea ice. Other embodiments of the invention will prove useful in detecting and mapping oil films and emulsions at sea, oil spills in arctic waters, tar balls on beach sand, and damage to wetlands from oil spills. The embodiments of the invention described herein are suitable for packaging in the form of, for example, hand-portable imaging sensors, ground vehicle-mounted inspection systems, vessel-mounted sensing systems, airborne surveying systems, relocatable trailer-mounted and fixed-site monitoring systems.

DRAWINGS—FIGURES

The patent or application file contains at least one drawing executed in color. Copies of this patent or patent application publication with color drawing(s) will be provided by the Office upon request and payment of the necessary fee.

FIG. 4A illustrates an example of real-time video imaging of natural gas exiting a 10 mm orifice from a pipe pressurized at a low levels of only ¼ psig in a mild crosswind.

FIG. 4B illustrates an example of real-time video imaging of methane jets emanating from a loosened hammer union pressurized to 500 psig in a 9 kph crosswind.

FIG. 4C illustrates an example of real-time imaging of ground surface emissions due to an underground natural gas pipe leak beneath a street in the Boston area.

Figure 8A:
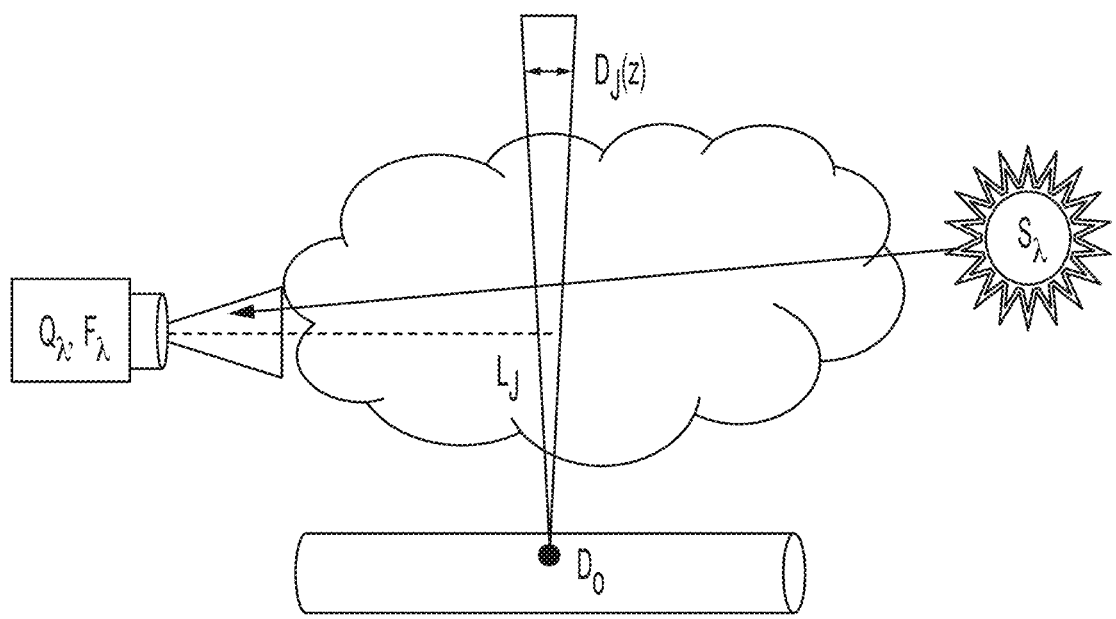

FIG. 8A diagrams the imaging geometry for leak detection with sunlight ahead of the leak in direct transmission, passing once through a gas jet towards the sensor.

Figure 8B:
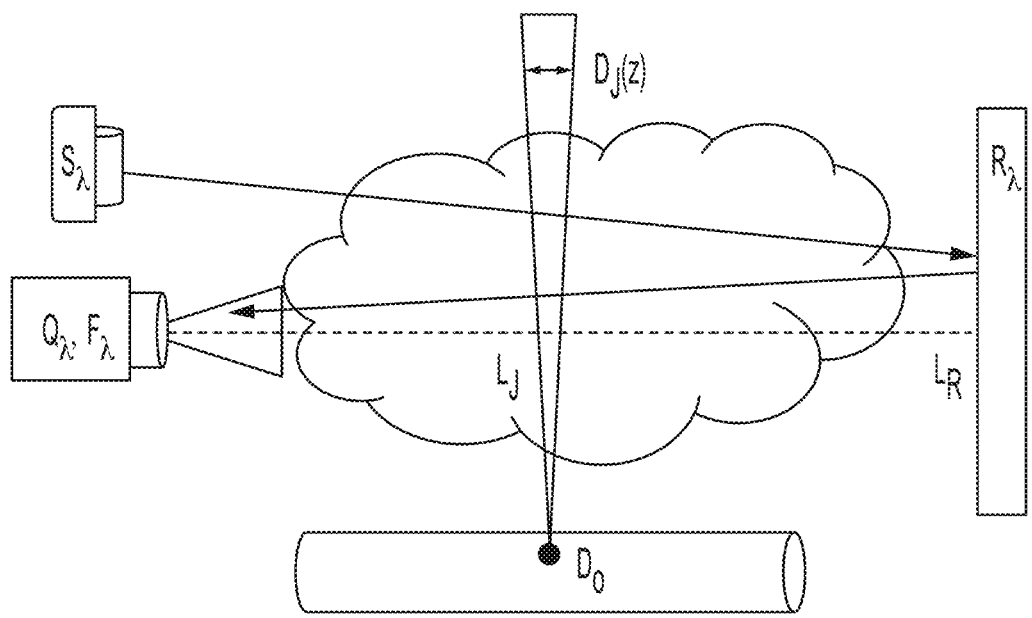

FIG. 8B diagrams the imaging geometry for leak detection with a source of artificial illumination from behind the leak (near the sensor), reflecting off a background material, passing twice through a gas jet and then to the sensor.

Figure 9A:
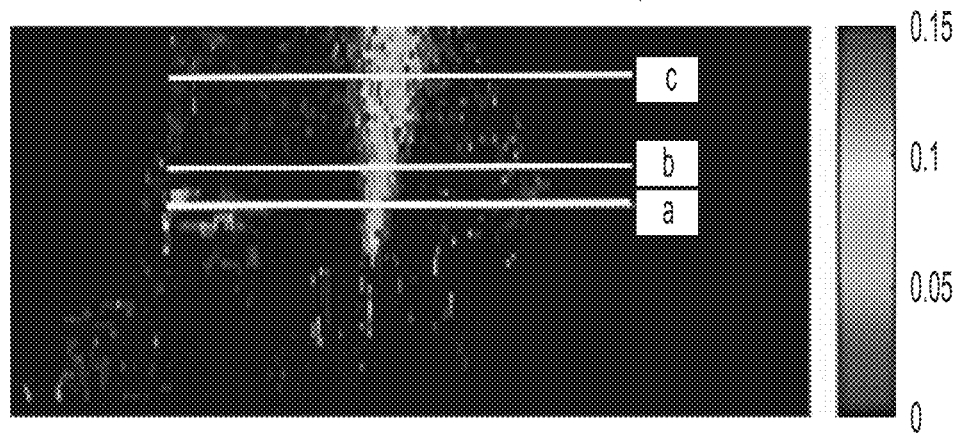

FIG. 9A shows a real-time absorption image of a methane gas jet exiting a 1 mm orifice from a test manifold pressurized to 1300 psig.

Figure 9B:
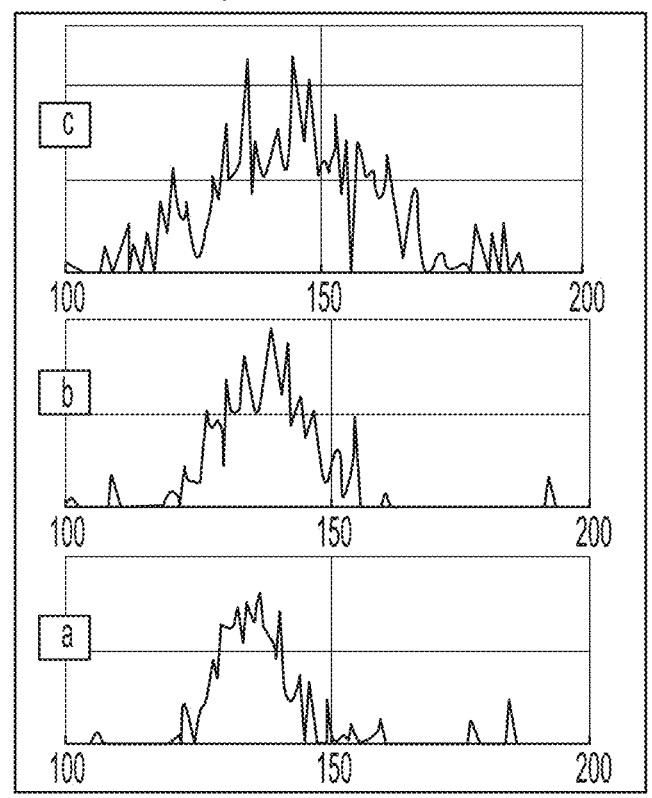

FIG. 9B shows three profiles of differential optical depth across the methane gas jet of FIG. 9A, corresponding to the pixel values sampled along the lines labeled a, b, and c.

Figure 10A:
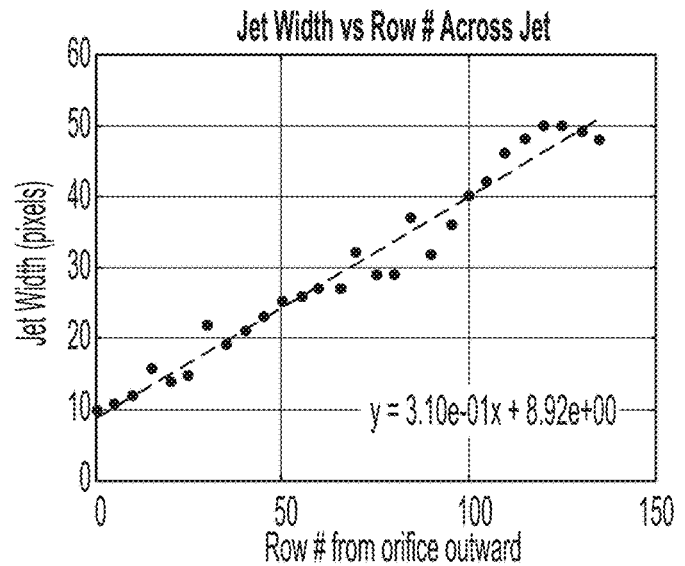

FIG. 10A shows a graph of the estimated jet width along the axis of the methane jet of FIG. 9A, and a least-squares linear regression to these data points.

Figure 10B:
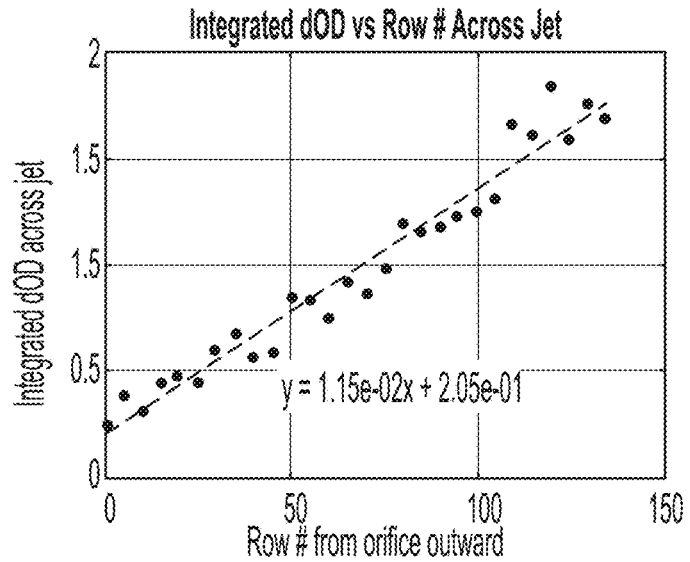

FIG. 10B shows a graph of the integrated differential optical depth across the width of the jet, along the axis of the methane jet of FIG. 9A, and a least-squares linear regression to these data points.

Figure 10C:
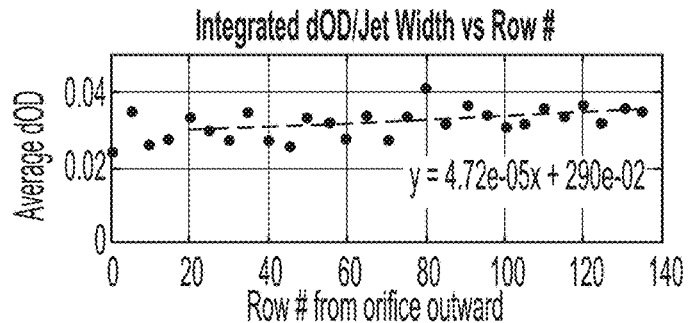

FIG. 10C shows a graph of the ratio of integrated differential optical depth to estimated jet width (i.e., the average differential optical depth) along the axis of the methane jet of FIG. 9A, and a least-squares linear regression to these data points.

Figure 11:
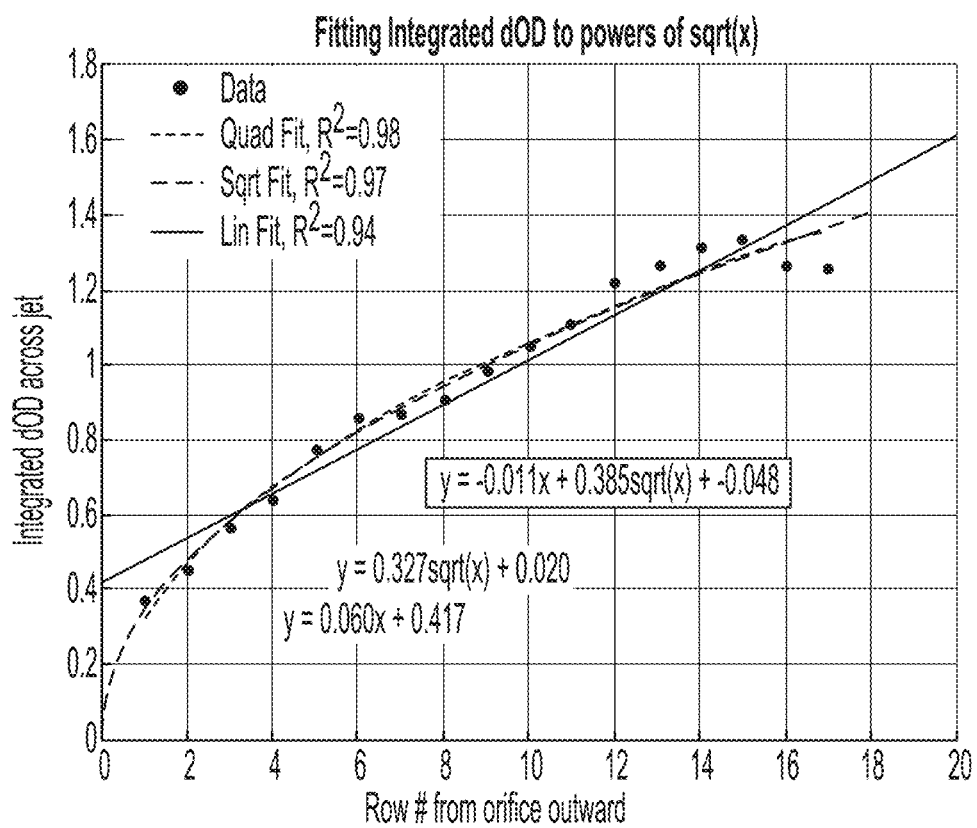

FIG. 11 shows a graph of the integrated differential optical depth across the width of a methane jet exiting a narrow slit orifice of width 50 microns and length 1 cm, and various least-squares regressions to these data points.

Figure 12A:
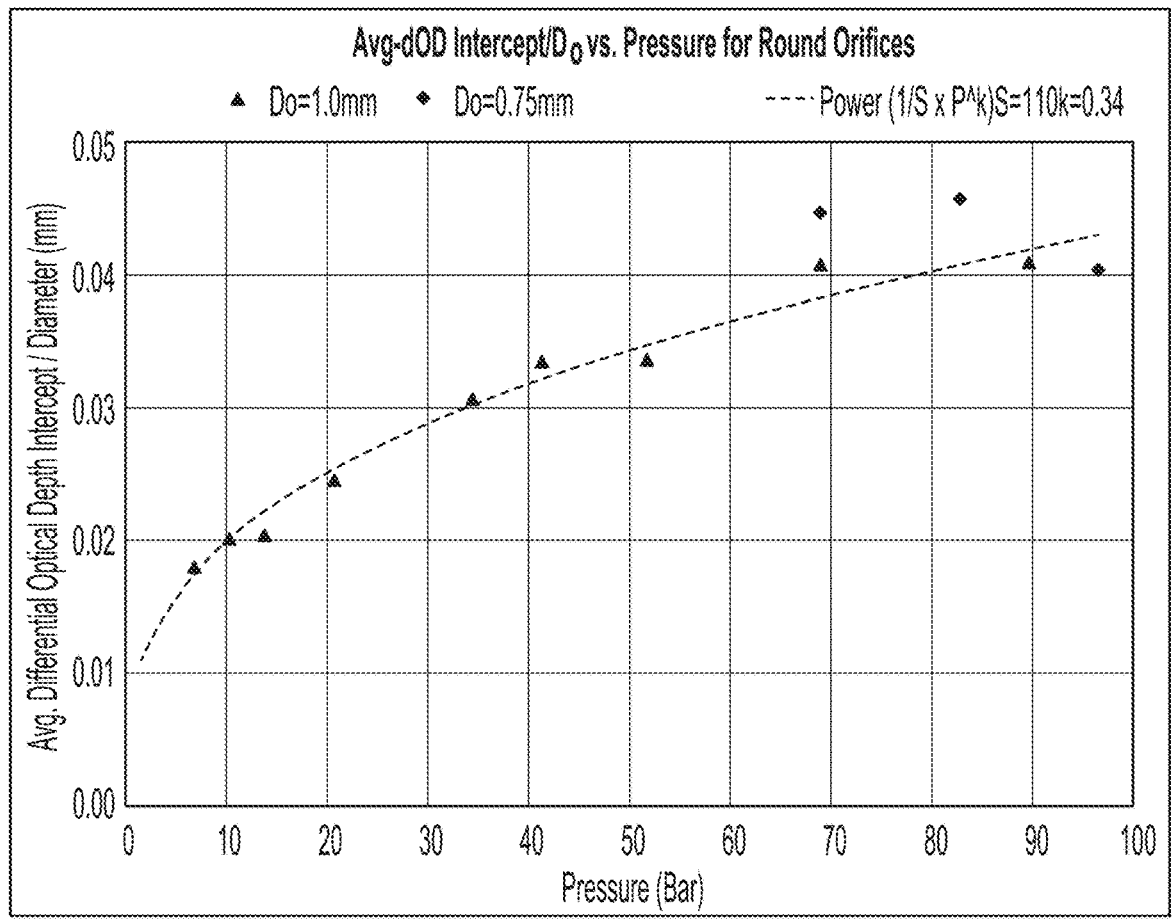

FIG. 12A illustrates for a set of experiments, a graph of the intercept value of average differential optical depth normalized by orifice diameter vs. the internal pressure driving a methane jet from orifices of 1 mm and 0.75 mm, and compares the data to a smooth power-law curve.

Figure 12B:
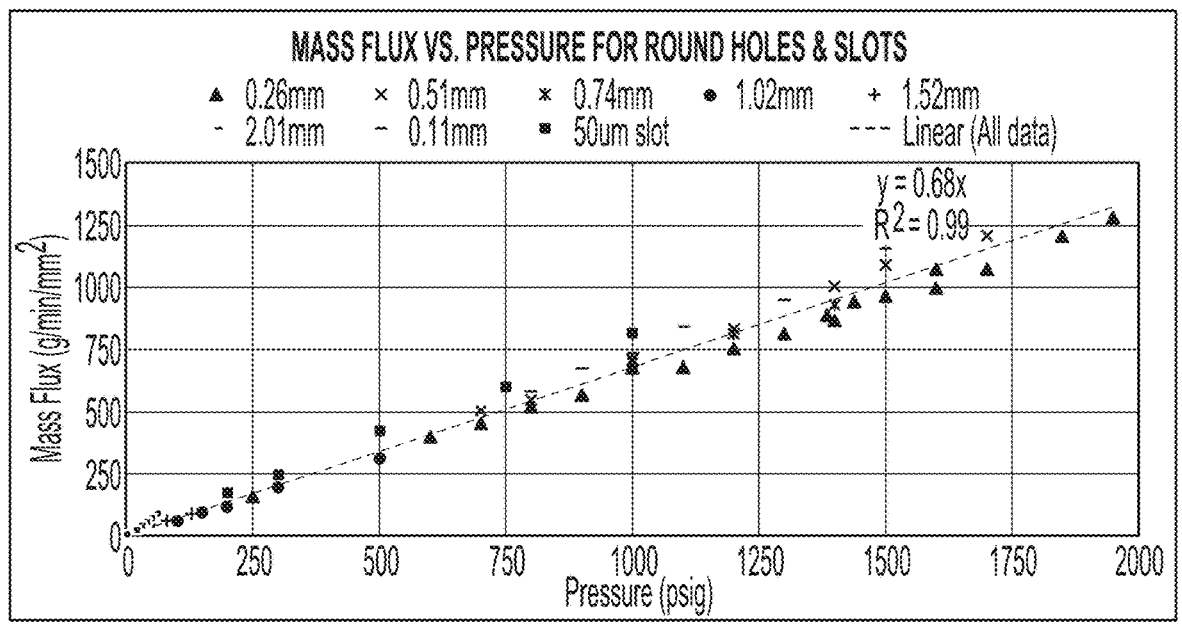

FIG. 12B illustrates data from an extensive set of experiments of methane exiting round and slit orifices of various sizes across a large range of pressures. The graph shows the measured mass flux per unit area of orifice vs. the internal pressure driving the methane jet, and a least-squares linear regression to these data points.

Figure 13A:
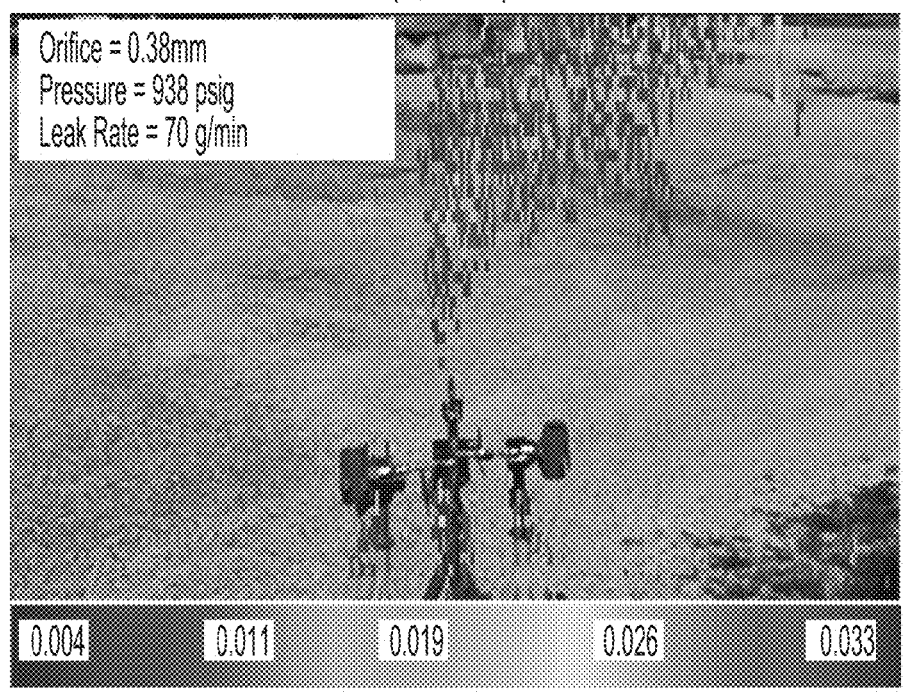

FIG. 13A illustrates an outdoor test setup used for imaging and estimating leak rate (mass outflow) of methane exiting round orifices under pressure in a crosswind in sunlight, in which the mass flowing into the release manifold is measured.

Figure 13B:
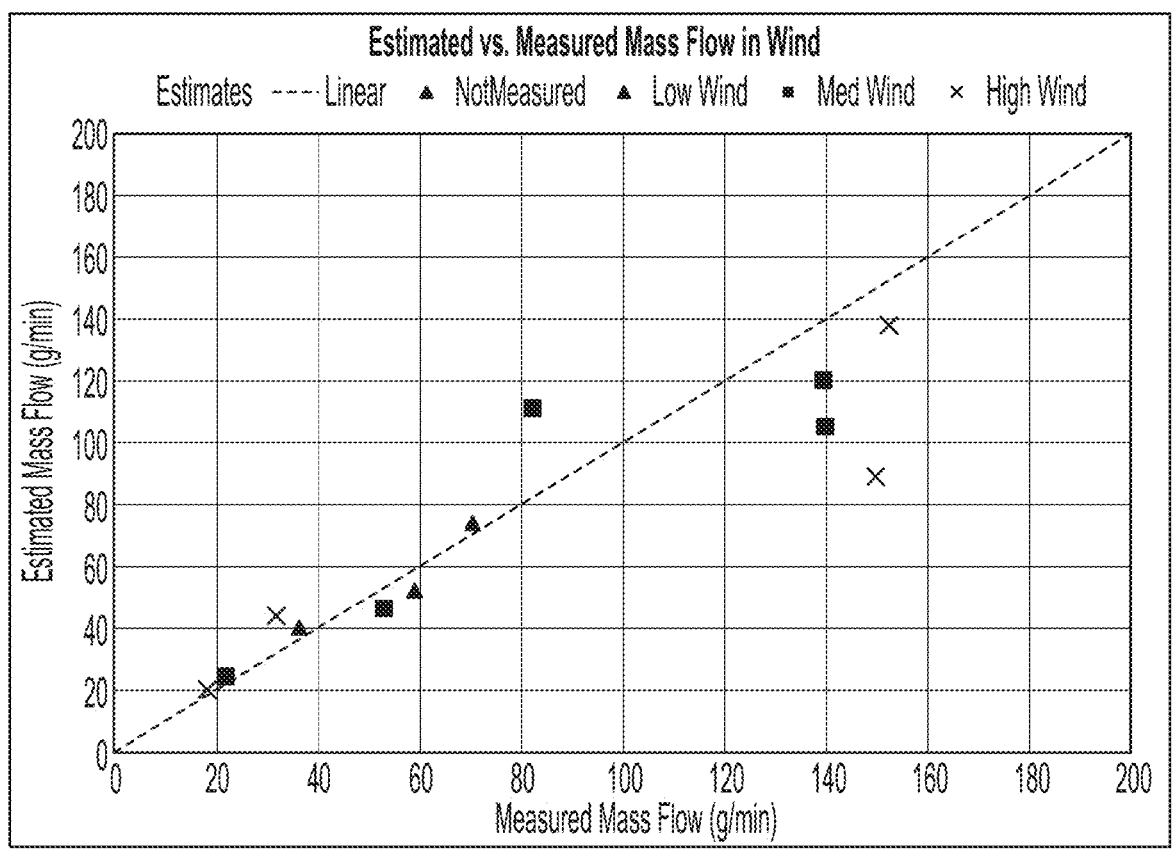

FIG. 13B shows a graph of estimated mass outflow compared to the measured mass inflow for twelve experiments using the test setup shown in FIG. 13A.

Figure 14A:
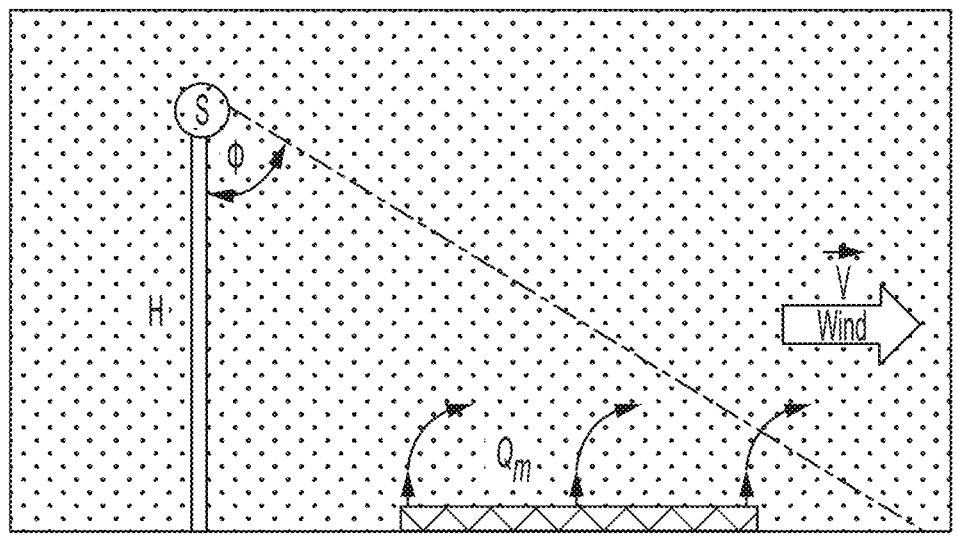

FIG. 14A illustrates (side view) geometry of an elevated LIQS sensor imaging ground surface gas emission in the presence of ground-level winds.

Figure 14B:
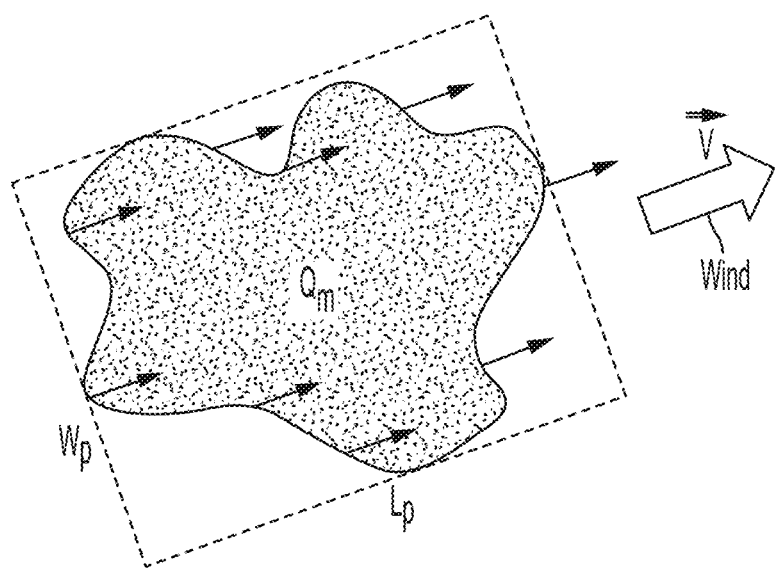

FIG. 14B illustrates (plan view) geometry of gas emission from a surface patch in the presence of ground-level winds.

DETAILED DESCRIPTION OF THE INVENTION

Principals of Gas Absorption Imaging

This invention detects gas leaks via differential absorption imaging spectroscopy in the range 1.0 to 2.6 microns, exploiting spectral features of hydrocarbons in the short-wave infrared (SWIR) region, primarily in the wavelength range of 2.0 to 2.5 microns. These wavelengths are not typically associated with those in the thermal emission regions of the mid-wave infrared (MWIR) and long-wave infrared (LWIR) for objects at terrestrial temperatures. Appreciable thermal emission at around 2.0 microns requires objects at temperatures of around 1000° C. Instead, this invention relies on illumination sources like natural sunlight and lamps of color temperature near 1000° C. Thus, the invention can detect hydrocarbons at the same temperatures as their backgrounds by using external illumination instead of thermally emitted light.

Figure 1A:
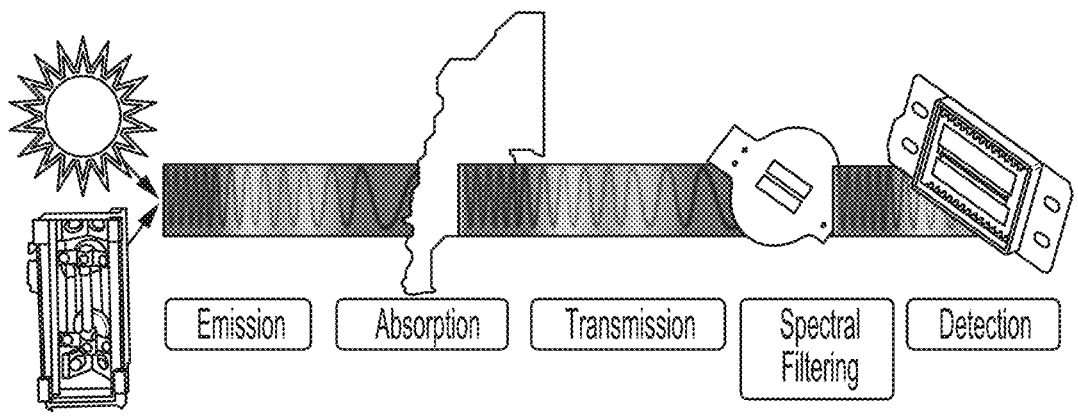
FIG. 1A illustrates the physical principles that underlie multispectral absorption imaging for natural gas detection.

The principals underlying non-thermal infrared multispectral imaging of a gas leak are shown in FIG. 1A. SWIR radiation from the sun or broadband artificial illumination, directly or in reflection off background objects, transmits through the ambient atmosphere, passes through a gas jet or plume emanating from a source such as for example a leak, continues towards the sensor where it is filtered into multiple spectral bands and detected on a photo-detector array that is sensitive to SWIR photons. Both the atmosphere and the gas absorb some of the light at wavelengths characteristic of the materials that comprise these media. In the case of natural gas the primary absorber is methane, while for the atmosphere the primary absorbers are water vapor and other ambient gases that may include methane as well as carbon dioxide. Incident light is also scattered out of the transmission path by particulates in the atmosphere and the gas leak itself. Light that is absorbed by the gas is subsequently reemitted in all directions, resulting in a reduction of light at characteristic wavelengths that is transmitted in the direction from the light source towards the sensor.

Figure 1B:
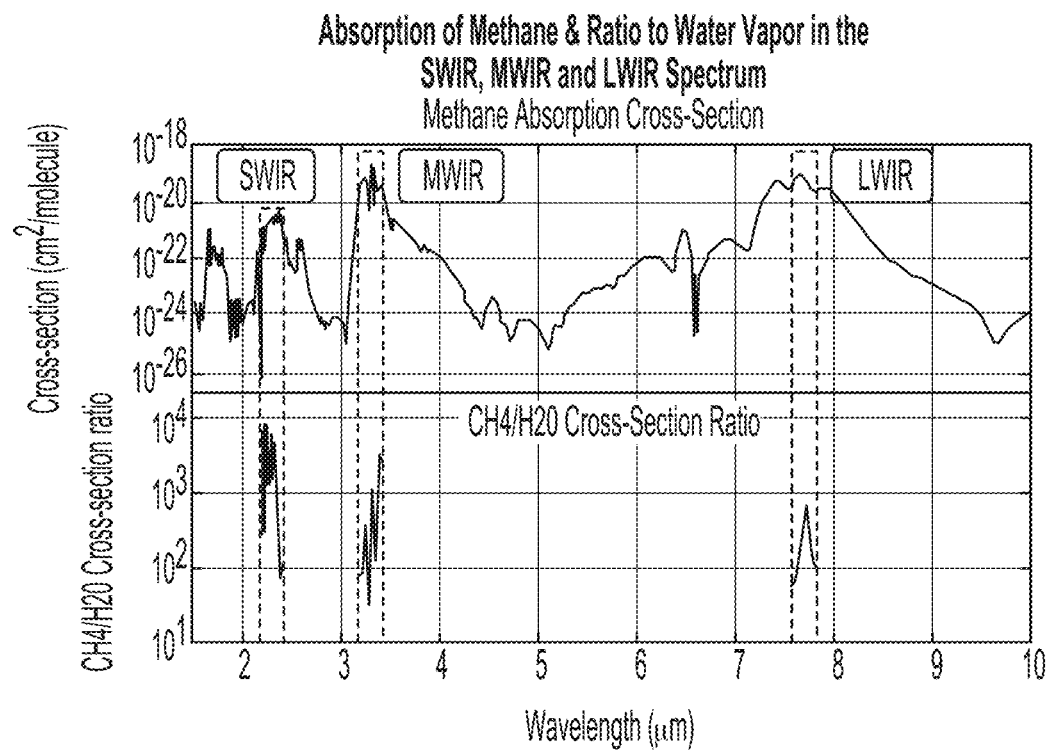
FIG. 1B illustrates the methane spectrum in the infrared region from 1.5 to 10 microns, its primary spectral absorption features in the short-wave, mid-wave, and long-wave infrared regions, and the ratio of these methane absorption features to the corresponding water-vapor absorption features.

When imaging methane and other hydrocarbons, it is common to exploit their strong features in the MWIR and LWIR, as the absorption in those spectral regions is greater than in the SWIR. However, it is important to consider the effects of water vapor absorption by the intervening atmosphere. In most applications, the physical extent of a gas jet, plume or cloud is small compared to the length of atmosphere that the light will propagate through on its way to the sensor. Thus, appreciable absorption may occur at wavelengths characteristic of water vapor, depending on the humidity of the air or the presence of fog or steam in optical field-of-view. It is therefore important to consider the relative absorption of methane to water vapor at the wavelengths that characterize methane. FIG. 1B illustrates this by plotting the methane absorption cross-section, and the ratio of water vapor to methane absorption cross-sections in narrow spectral bands where methane possesses strong spectral features, shown here on semi-logarithmic scales for wavelengths from 1.5 to 10 microns. It is clear that, despite the relatively weaker absorption cross-section for methane in the SWIR compared to the MWIR and LWIR, it has significantly higher absorption ratio to water vapor in the SWIR. Thus, for imaging gas in the presence of humidity or fog or steam, the SWIR region has particular advantage over both the MWIR and LWIR spectral regions. For many applications, this is an advantage, despite the lower absorption cross-section in the SWIR.

Figure 2A:
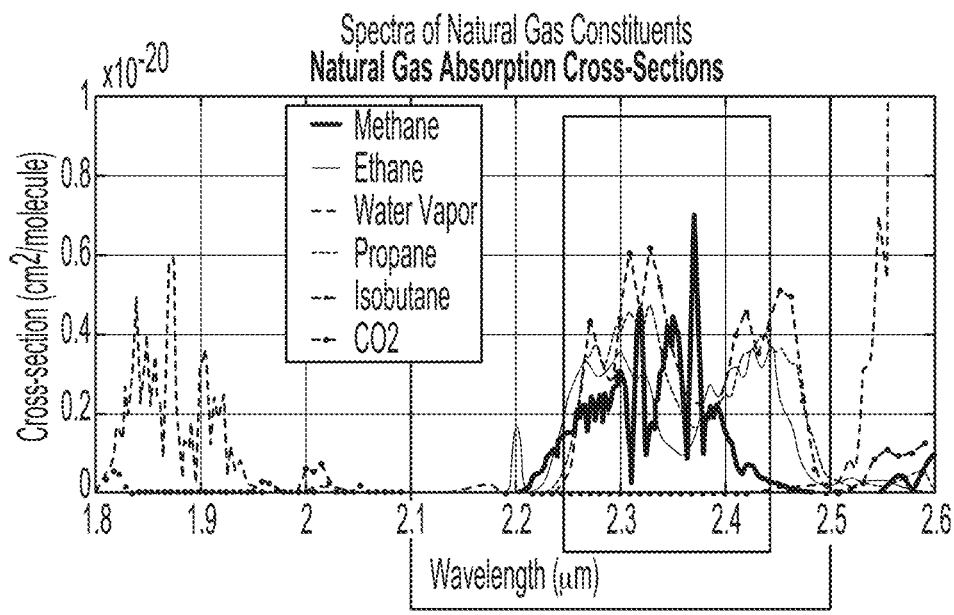
FIG. 2A illustrates the short-wave infrared spectra of the primary constituents of natural gas—methane, ethane, propane, butane, and carbon dioxide, as well as the spectrum of water vapor.

FIG. 2A shows a plot of absorption cross-section (on a linear scale) in the SWIR spectrum from 1.8 to 2.6 microns, for the various constituents comprising natural gas: methane, ethane, propane, butane, and carbon dioxide, as well as for water vapor. From FIG. 2A it can be seen that the hydrocarbons possess broad feature complexes from 2.2 to 2.5 microns with much overlap in the range of 2.2 to 2.4 microns. Methane can be separated from the other hydrocarbons by its reduced absorption in the 2.4 to 2.5 micron range. It is also apparent that the constituents of natural gas have spectral features in the SWIR that lie between the strong water vapor features below 2.0 microns and above 2.5 microns. As is well known in the art, similar absorption features are present in the SWIR for liquid crude oil, oil-water emulsions, asphalt and tar.

Figure 2B:
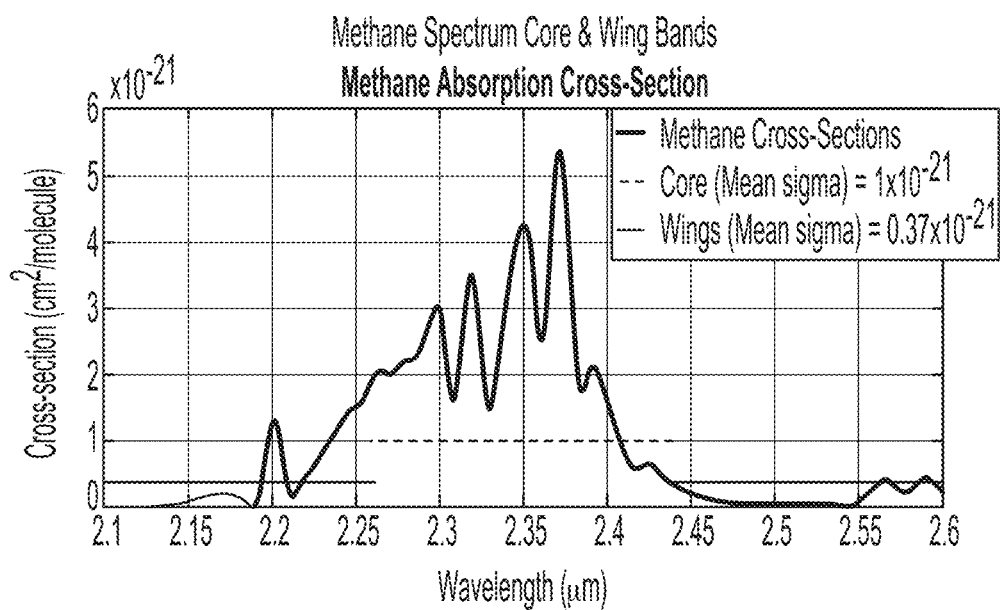
FIG. 2B illustrates the detailed methane spectral features in the range 2.1 to 2.6 microns, and its decomposition into a Core Band and Wings Band, along with the value of the average absorption cross-sections for this choice of Core and Wings Bands.

In order to detect and quantify the hydrocarbons present in natural gas, it is advantageous to use multiple spectral bands in the SWIR. This can be accomplished using spectral filters designed to selectively transmit preferred wavelength bands while rejecting other SWIR radiation. Such spectral filters can be narrow bandpass filters, broadband filters, notched filters, edge filters, and combinations of such filters. For example, to preferentially detect methane, the primary constituent of natural gas, the invention utilizes a minimum of two spectral bands; one called the Core Band which spans the spectral feature complex from approximately 2.25 to 2.45 microns (200 nm bandwidth), and the other called the Wings Band (serving as a reference band) which spans an interval of approximately 100 nm to either side of the Core Band. These spectral intervals are shown as the rectangular boxes in FIG. 2A. The average absorption cross-section across the Core and Wings Bands are plotted over the methane spectrum in FIG. 2B. By imaging in these two bands, the presence of methane can be both detected and quantified in terms of column density of methane. As is well known in the art of spectral image processing, other SWIR spectral bands can be selected to preferentially detect and quantify the other constituents of natural gas shown in FIG. 2A and related volatile organic compounds of interest in gas and oil production. The exact location and extent of any of these bands is not critical to enabling a functional sensor, as long as they span regions both on and off the strong spectral features of the gas of interest. In order to quantify the column density of gas present at each pixel in the imagery, and account for absorption by trace gases in the atmosphere, it is shown below that comparison between regions with gas present and gas absent is preferred, and this is achieved through proper on-site adaptive calibration of the system before inspecting for gas leaks.

Prototype Gas Imaging Sensor

The invention described here has been reduced to practice by building functional prototypes of a multispectral video imager and a scan imager for methane imaging, detection and quantification The prototype dual-band video sensor images at 20 frames per second and displays gas absorption imagery overlaid on color visible imagery of the scene on a touch-screen user display. The prototype system is hand-portable and interfaces to external networks via both wireless and wired interfaces. The prototype 6-band scan sensor creates imagery of gas over a programmable and variable field-of-regard, by combining raster scanning with super-resolution image processing. The flexibility of switching among a variety of scan patterns enables this sensor to support both gas safety applications and emissions monitoring applications, in a cost-effective manner. This scan imager is suitable for mast-mounting to overlook wide-area installations, using a programmable pan-tilt unit to effect scanning. An alternative embodiment replaces the pan-tilt unit with scanning mirrors or a combination of scanning mirror and rotating optics, to enable compact packaging for a hand-portable gas imaging and quantification camera.

Figure 3:
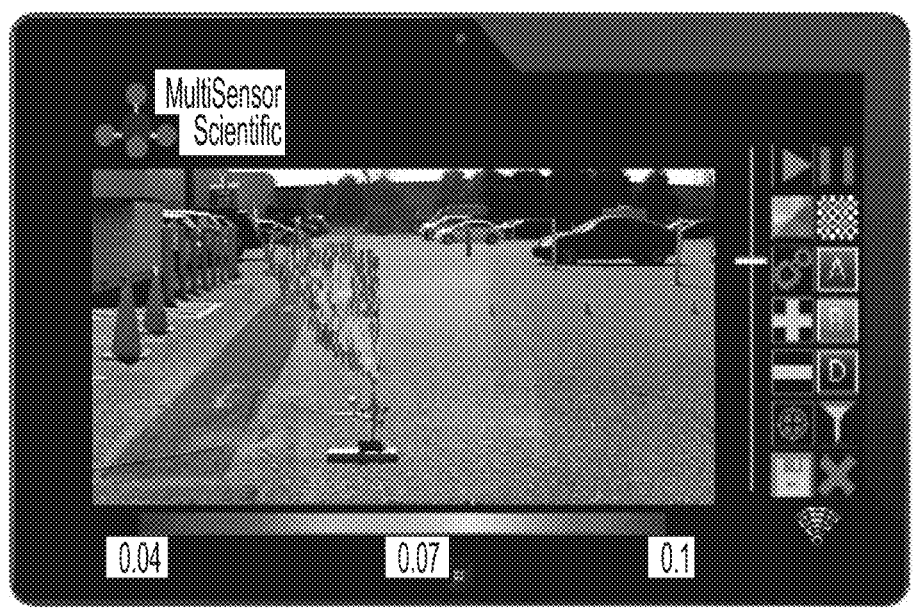
FIG. 3 shows a prototype user interface for a gas imaging sensor implemented on a touch-screen tablet, displaying a methane gas jet exiting a 1.5 mm orifice at 130 psig.

FIG. 3 illustrates a prototype graphical user interface for the video gas imager, showing touch-screen controls of the sensor and displaying an image of natural gas emanating from a 1.5 mm round orifice at a pressure of 130 psig (pounds per square inch gauge), taken outdoors in sunlight. The color rendering of the gas jet absorption corresponds to pixel-level differential optical depth between the Core and Wings Bands, which can be converted to column density of methane and expressed in a variety of common units (molecules/cm$^2$, % LEL-meters, ppm-meters). FIG. 4A is another example of gas imaging, showing a natural gas plume emanating from a 10 mm round ball valve orifice inside a 16 mm pipe at a low (household) gas pressure of 14 psig in a mild crosswind, outdoors using artificial illumination. This low-pressure release of natural gas is dominated by the buoyancy of methane in air, and accelerates upwards under gravity as a buoyant turbulent plume. FIG. 4B shows a pair of momentum dominated methane jets driven out of a loose threaded hammer union by high internal pressure of 500 psig; they form turbulent gas jets a short distance from slit-like orifices. By exploiting the self-similar dynamics of gas jets and plumes, it is shown how this absorption imagery can be used to estimate the diameter of the release orifice and the mass flux of methane from the hole. A final example of gas imaging is shown in FIG. 4C, where natural gas is leaking from an underground pipe in municipal gas infrastructure in Boston, Mass. By the time the gas percolates up through the soil, it is approximately the same temperature as the ground itself. The prototype system can image the gas emissions from the surface in sunlight as shown, or alternatively using artificial illumination (possibly mixed with sunlight) from above reflecting off the ground, which is absorbed as it passes through the gas twice. FIG. 4C illustrates the patchy nature of ground surface emissions, with gas emerging from manholes, storm gratings, cracks in road asphalt and concrete sidewalks, as well as along the side of the road where the asphalt meets dirt and grass. All of these surface emissions may be due to a single leak in a pipe at the bottom of the hill near the end of the street. The spatial distribution of surface leak patches can be useful in bounding the actual leak location in the underground pipe.

Imaging Sensor Embodiments

Several different embodiments of SWIR imaging sensors for hydrocarbon imaging are described next. There are several different semiconductor materials that can be used to fabricate the basic photo-detector sensitive to the SWIR spectrum of light from approximately 1.0 to 2.6 microns, with a dark-current that can be suitably reduced by thermo-electric cooling. These include so-called extended-response indium gallium arsenide (extended-InGaAs) commonly grown on an indium phosphide (InP) lattice-mismatched substrate, and the recently developed type-II quantum wells made from alternating layers of InGaAs and gallium arsenide antiminide (GaAsSb) grown on an InP lattice-matched substrate. These two materials have different spectral response characteristics, but both can be used for detecting the hydrocarbons that comprise natural gas, and in particular, methane as well as VOCs. They also have different manufacturing yields due to their lattice structures. Thus, extended-InGaAs photo-detectors are only available as discrete photo-detectors and one-dimensional arrays but not as two-dimensional arrays, while type-II InGaAs/GaAsSb photo-detectors have been successfully fabricated and demonstrated as two-dimensional arrays. Mercury cadmium telluride (MCT) is a common infrared detector material that can also be used for imaging in the extended SWIR; however, its high dark-current requires cryogenic cooling with, for example, a Stirling engine to achieve useful signal-to-noise ratios.

Figure 5A:
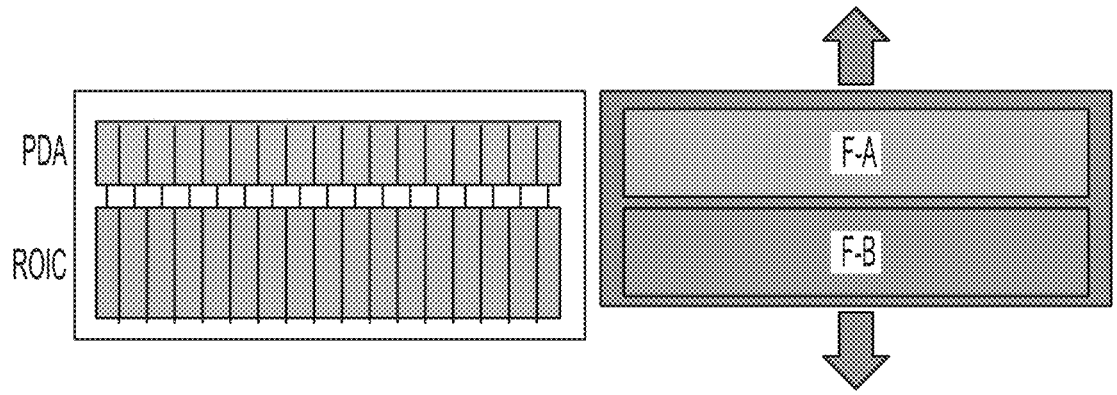
FIG. 5A is a one-dimensional photo-detector array with its read-out circuitry, together with a pair of spectral filters that overlays the detector array and alternates between each of the two filters covering the detector array.
Figure 5B:
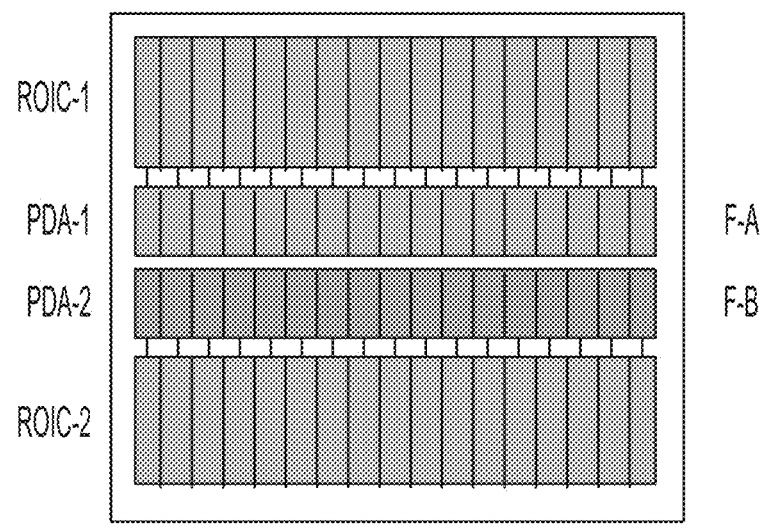
FIG. 5B is a pair of one-dimensional photo-detector arrays, each with its own read-out circuitry, and each with a different spectral filter positioned over it.

There are several embodiments of photo-detector arrays in combination with multiple spectral filters that yield a suitable sensor for use in a gas leak imaging and quantification system. FIGS. 5A and 5B illustrate the use of one-dimensional SWIR photo-detector arrays in combination with two spectral filters called F-A and F-B, which can be used to create the Core Band and Wings Band filters for methane detection or other hydrocarbons of interest. A one-dimensional (i.e., linear) 2.5 um-SWIR InGaAs array with 512 detectors is used in the functional prototype methane gas imager. The configuration of FIG. 5A shows a single linear array of photo-detectors with its read-out integrated circuit (ROIC) together with a pair of filters in a frame that is designed to overlay the photo-detector array and alternate between the filters F-A and F-B positioned in front of the detector array. In this example, the photo-detector array and its ROIC are mounted on a small thermo-electric cooler and enclosed inside a hermetically sealed package with a transparent window located above the photo-detectors. The alternating filter assembly is positioned outside the package so that each filter overlays the window as the filters alternate in position. This configuration uses a mechanical means to move the respective filters into place at a sufficiently fast rate to support the desired imaging requirements. Other means of alternating spectrally separated bands of light onto a linear detector array are also possible. The prototype gas imager operates at 20 frames/second.

FIG. 5B shows another configuration of one-dimensional SWIR photo-detector arrays and filters, where two separate linear arrays with their own ROICs are configured in parallel layout on a common thermo-electric cooler inside a hermetically sealed package with a window located above the pair of photo-detector arrays. Filters F-A and F-B are mounted either in a frame or glued directly to the window, each filter being fixed in place and located above one of the photo-detector arrays. This configuration eliminates the need to mechanically move the filters rapidly and lends itself to higher frame rates. This configuration of two parallel linear arrays of photo-detectors can also be used with an alternating or otherwise changeable filter array such that a new pair of filters is moved into place to overlay the detector arrays. For example, a four-band imager would be created from a dual-linear detector array with alternating pairs of filters in a quad-filter frame, and could, for example, support separate detection and quantification of methane and volatile organic compounds or methane and carbon dioxide.

Figure 6A:
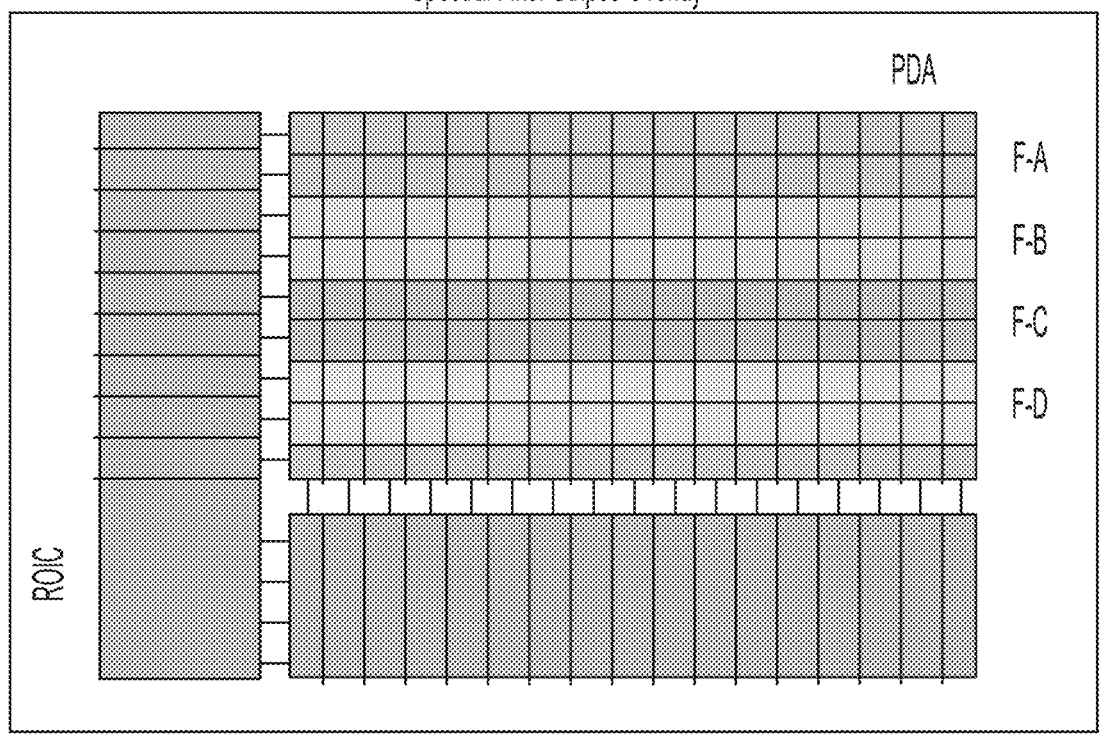
FIG. 6A is a two-dimensional photo-detector array and its read-out circuitry, with four different spectral filters, each filter overlaying one or more rows of detectors.

FIG. 6A illustrates the use of a two-dimensional SWIR photo-detector array and ROIC, where an array of four filters, F-A, F-B, F-C, and F-D are configured as stripes that overlay the detector array. The filter stripes can extend across most of the array, with each stripe covering one or more rows of detectors. The detector array and ROIC is to be mounted on a thermo-electric cooler and enclosed in a hermetically sealed package with a transparent window over the detector array. The filter stripes can be configured into an array as a mosaic of individual filters in a frame, or fabricated as a monolithic array, and it is clear that more than four different filters can comprise the array. Two-dimensional 2.5 um-SWIR type-II InGaAs/GaAsSb imaging arrays of size 320×256 pixels are now commercially available. This configuration can be viewed as a collection of many linear arrays covered by a set of spectral filters.

Figure 6B:
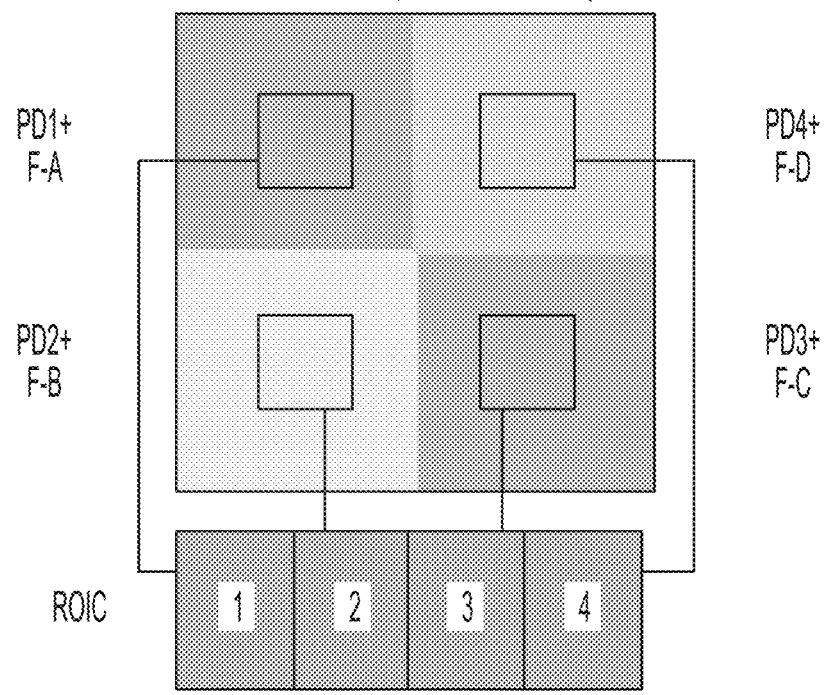
FIG. 6B is an array of four discrete photo-detectors with their individual read-out circuits, each detector covered with a separate spectral filter island. The spectral filters form a spectral filter mosaic.

FIG. 6B shows a configuration of four discrete SWIR photo-detectors, PD1, PD2, PD3, and PD4, arranged in a 2×2 array, each with its own analog read-out circuit and (possibly shared) analog-to-digital converter, and each covered with a separate spectral filter island. In practice, the four discrete photo-detectors are to be mounted on a common thermo-electric cooler and enclosed in a hermetically sealed package (e.g., a TO-8 "transistor-outline" metal can) with a transparent window. The spectral filters can be assembled from discrete filters into a spectral filter mosaic, or fabricated as a monolithic array of filter islands, and located outside the window aligned with the photo-detectors below. With the appropriate lens, this configuration forms the equivalent of a single multi-spectral SWIR pixel. This configuration can clearly be extended to more or fewer discrete photo-detectors, each with its own spectral filter. A minimum of two spectrally filtered photo-detectors is required to construct a scanner that can image and quantify gas emissions. This same type of spectral filter mosaic can also be combined with the two-dimensional photo-detector array shown in FIG. 6A, whereby each filter island of the mosaic overlays a small two-dimensional sub-array of even smaller pixels. Upon read-out of the entire detector array, each sub-array of pixels corresponding to the same filter island can be combined into a macro-pixel. This configuration trades off reduced spatial resolution for increased signal in a two-dimensional array of very small photo-detectors.

All of the multi-spectral SWIR detector configurations described and shown in FIGS. 5 and 6 utilize additional scanning and focusing optics in order to create two-dimensional spectral imagery from which a gas detection imager can be created. As is known to one of ordinary skill in the art, all the detector embodiments shown in FIGS. 5 and 6 lend themselves to packaging in hand-held systems, and can also be configured to operate on moving platforms such as ground vehicles, airborne rotorcraft and fixed-wing platforms, ships, rotating mast-mounted systems, and translating rail-mounted systems.

Gas Imaging Sensor Systems

Figure 7A:
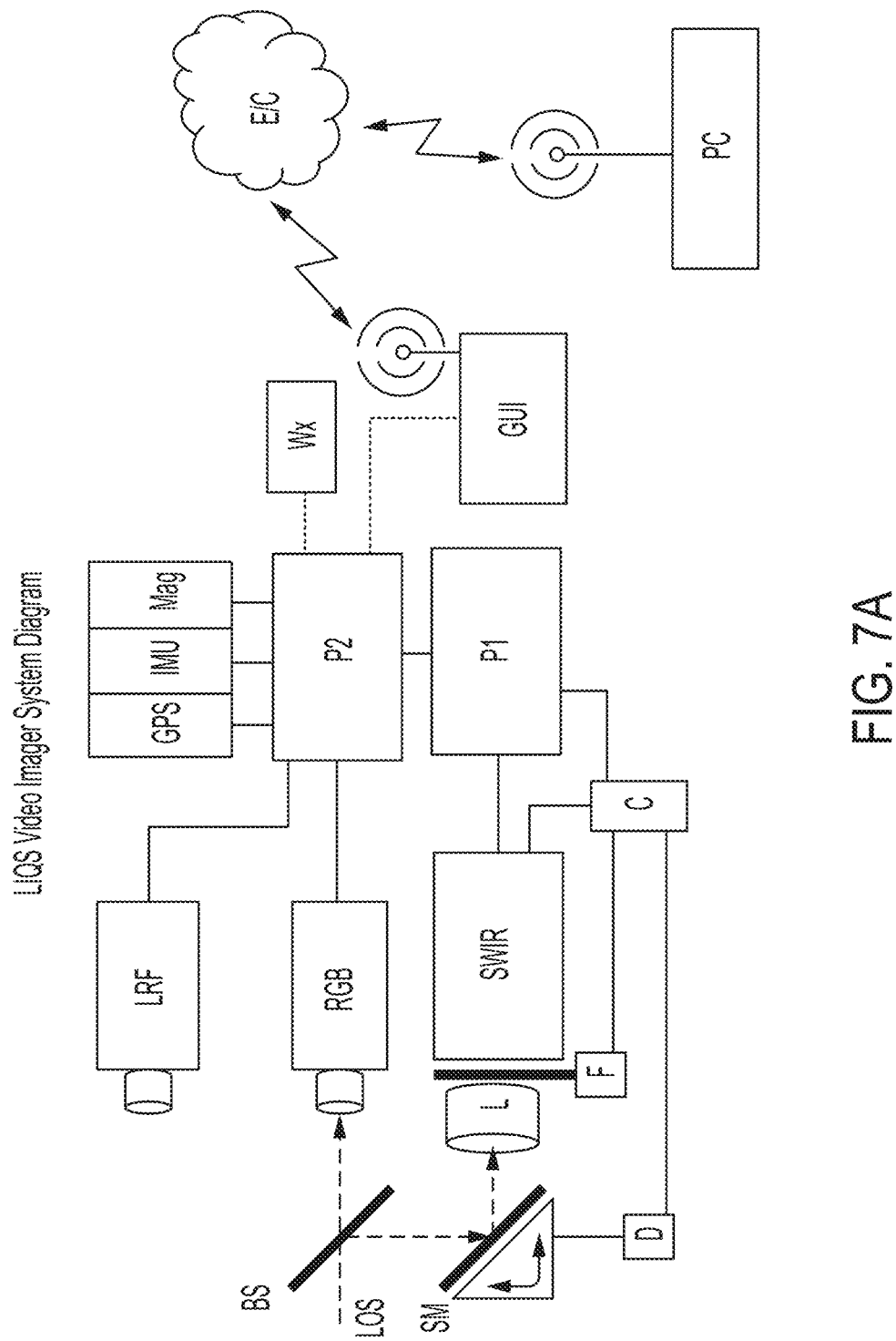
FIG. 7A is a system diagram of the video leak imaging and quantification sensor system.

FIG. 7A illustrates a first system diagram for the video gas imaging sensor system. Beginning with the SWIR camera (SWIR), it consists of one of the SWIR photo-detector arrays (linear, dual-linear, or two-dimensional) as shown in FIGS. 5A, 5B and 6A, together with its corresponding read-out circuitry and video timing circuitry. This SWIR camera has a SWIR lens (L) that is transmissive to at least the spectral range spanning the wavelengths of interest to sense the hydrocarbon features, approximately 1.0 through 2.6 microns. Positioned between the SWIR lens (L) and the SWIR camera (SWIR) is the spectral filter array positioner (F) which may include a motor and/or mechanical fixture to properly locate the correct filter(s) in front of the photo-detector array(s) during the exposure of each frame. This combination of SWIR detector array plus filter array corresponds to the various embodiments as shown in FIGS. 5A, 5B, and 6A. The SWIR imaging sub-system also includes a scanning mirror (SM) which sweeps the scene across the spectrally filtered photo-detector array so as to create a two-dimensional field-of-regard. The scanning mirror (SM) is typically a one-dimensional scanner that sweeps in a directional perpendicular to the orientation of the filters positioned over one-dimensional detector arrays or the stripes over the two-dimensional detector array. An electronic driver (D) controls the scanning mirror (SM). Synchronization between the scanning mirror (SM), filter positioner (F), and SWIR camera (SWIR) is provided by a micro-controller (C). Two-dimensional image assembly is performed on a micro-processor (P1).

TABLE 1

Definitions of abbreviations used in FIG. 7A.

| Abbreviation in FIG. 1C | Definition |
|---|---|
| SWIR | SWIR photodetector array with read-out imaging electronics |
| L | Lens for SWIR photo-detector array (located in front of filters) |
| RGB | Color visible micro-camera with lens |
| LRF | Laser Range Finder |
| LOS | Line of sight from coincident optical axes of imagers |
| BS | Beam Splitter (dichroic) |
| SM | Scanning mirror |
| D | Driver electronics for scanning mirror |
| F | Filter changer (as required for moving filter holder) |
| C | micro-Controller for synchronization signals |
| P1 | micro-Processor #1 (real-time SWIR processor) |
| P2 | micro-Processor #2 (all other sensor and GUI requests) |
| GPS | Global Positioning System receiver |
| IMU | Inertial Measurement Unit (6 degrees-of-freedom) |
| Mag | Magnetometer compass |
| Wx | Weather sensors (T, P, RH, wind speed & direction) |
| GUI | Graphical User Interface on touchscreen tablet |
| E/C | Ethernet/Cloud |
| PC | Personal Computer remotely running system via cloud |

Figure 7B:
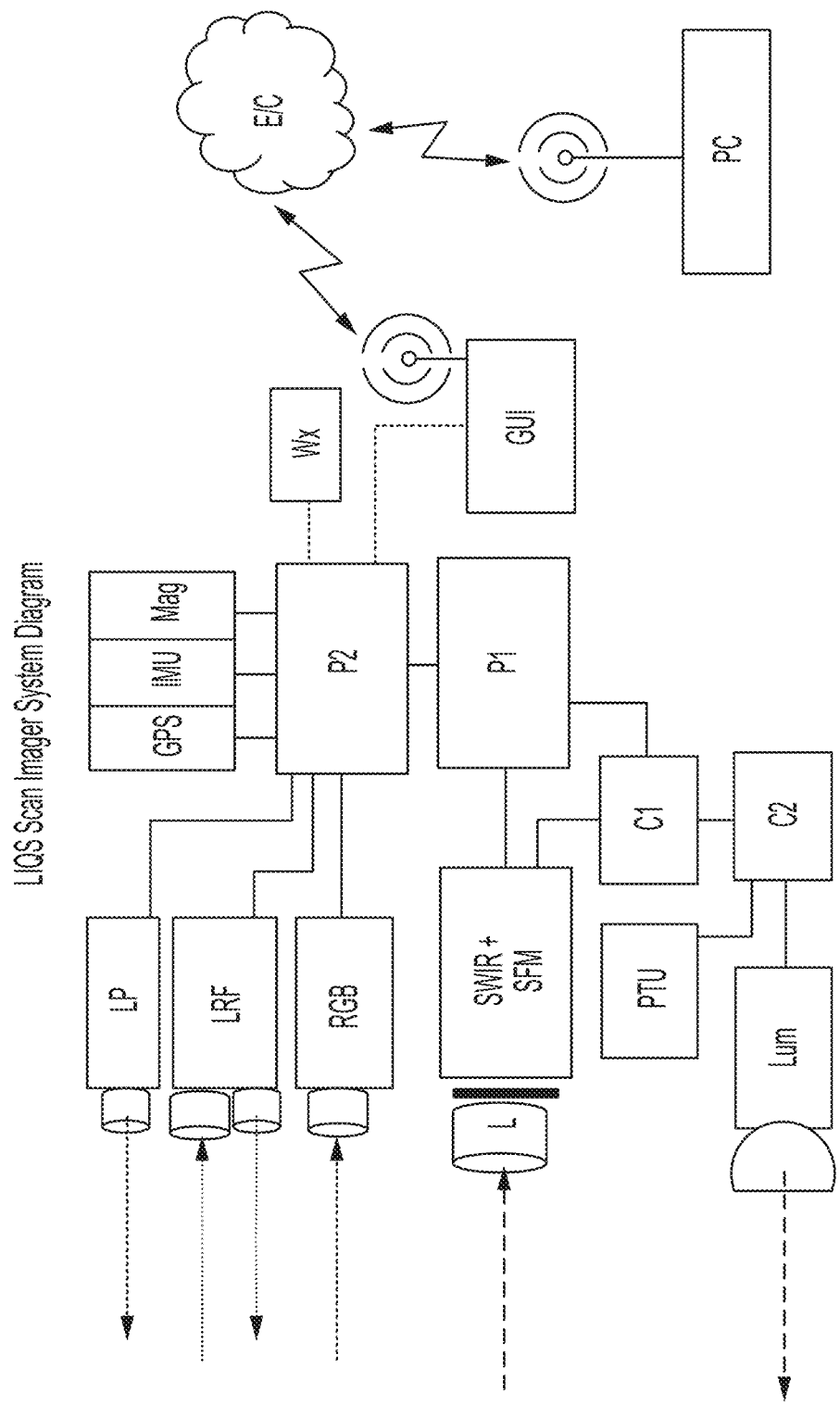
FIG. 7B is a system diagram of the scan leak imaging and quantification sensor system.

FIG. 7B illustrates a second system diagram for the scan gas imaging sensor system. In this case, the discrete photo-detectors and spectral filter mosaic (SFM) of FIG. 6B form a single multispectral pixel by means of a defocusing lens (L), and this sensor is scanned across the scene in two directions by mounting it atop a high-accuracy pan-tilt unit (PTU) controlled by micro-controller (C2). Two-dimensional imagery is created by raster scanning across a desired, and possibly variable, field-of-regard. In order to create imagery of higher resolution than that obtained directly by scanning this sensor with its own narrow field-of-view, it is useful to employ spatial over-sampling in combination with super-resolution image processing, which is widely discussed in the literature. Two-dimensional scanning can be accomplished in a compact configuration, for example, by a pair of scanning mirrors or a pair of rotating prisms. Two-dimensional imaging can also be achieved using a single scanning mirror combined with physical movement of the imaging sensor (e.g., translation or rotation in a direction perpendicular to the scan mirror motion) such as by mounting the sensor upon a moving platform (e.g., truck-mounted, airborne, rail-mounted) or rotating the sensor in a mast-mounted configuration.

TABLE 2

Definitions of abbreviations used in FIG. 7B.

| Abbreviation in FIG. 1D | Definition |
|---|---|
| SWIR | SWIR photodetector array with read-out imaging electronics |
| SFM | Spectral Filter Matrix located over SWIR detector array |
| L | Lens for SWIR photo-detector array (located in front of SFM) |
| RGB | Color visible micro-camera with lens |
| LRF | Laser Range Finder (near-IR) |
| LP | Laser Pointer (visible "red dot") |

TABLE 2-continued

Definitions of abbreviations used in FIG. 7B.

| Abbreviation in FIG. 1D | Definition |
|---|---|
| PTU | Pan-Tilt Unit scans sensors across site in two-dimensions |
| Lum | SWIR broadband illuminator to augment solar illumination |
| C1 | micro-Controller with A/D converter samples SWIR signals |
| C2 | micro-Controller controls PTU motion and illuminator brightness |
| P1 | micro-Processor #1 (real-time SWIR processor) |
| P2 | micro-Processor #2 (all other sensor and GUI requests/display) |
| GPS | Global Positioning System receiver |
| IMU | Inertial measurement unit (6 degrees-of-freedom) |
| Mag | Magnetometer compass |
| Wx | Weather sensors (T, P, RH, wind speed and direction) |
| GUI | Graphical User Interface on touchscreen tablet |
| E/C | Ethernet / cloud |
| PC | Personal computer remotely running system via cloud |

Each imaging sensor system of FIGS. 7A and 7B may also include one or more visible color (RGB) or black and white cameras, laser range finder (LRF) to measure distance from the sensor to a detected leak, global positioning system (GPS) sensor to determine sensor location (and indirectly leak location), inertial measurement unit (IMU) to sense linear and rotational accelerations including direction of gravity, magnetic sensor (Mag) to sense the earth's magnetic field acting as a compass, and/or weather sensors (Wx) to relay local atmospheric conditions including wind speed and direction, all of which is packaged together with one or more processors (P1, P2). In order to optically register the visible imagery with the SWIR imagery and resulting gas absorption imagery, as shown in FIG. 7A, a beam splitter (BS) is incorporated that is preferably dichroic, such that the incident light along the line-of-sight (LOS) is mostly transmitted through the beam splitter for visible wavelengths 0.4 through 0.7 microns, and mostly reflected for SWIR wavelengths 1.0 through 2.6 microns. The reflected SWIR light is subsequently reflected by the scanning mirror (SM) towards the SWIR lens (L) that focuses this light onto the SWIR camera (SWIR) behind the spectral filter assembly (F). Alternatively, as shown in FIG. 7B, in the absence of a beam splitter, the measured range to each SWIR sample can be used to correct the parallax offset between that SWIR sample and its corresponding location in the visible RGB image, using the known spacing of the SWIR, RGB, and LRF sensors.

As shown in FIGS. 7A and 7B, one processor (P1) is associated with the multispectral SWIR camera and is responsible for real-time or near real-time processing of the SWIR multispectral data to create the gas absorption imagery. A separate processor (P2) has a path for accepting the visible camera (RGB) imagery and triggers the other low-bandwidth sensors (LRF, GPS, IMU, Mag). This processor (P2) also communicates wirelessly (or wired) with an external weather sensor (Wx) and a graphical user interface (GUI) implemented on a touch-screen tablet computer. The tablet, in turn, provides wireless access to an Ethernet or data cloud (E/C), which in turn can be accessed by a remote personal computer (PC). This arrangement enables remote (PC) access and control of one or more gas imaging sensor systems. Finally, an artificial illuminator (Lum), as explicitly shown in FIG. 7B, is controlled by a micro-controller (C2) and incorporated to enable gas imaging in the absence of sufficient sunlight or for indoor locations. Alternative implementations are possible, such as for example (but not limited to) a configuration with:

- the display or the controls or the complete user interface physically attached to the imaging device,
- the display or the controls or the complete user interface physically remote from the imaging device,
- the user interface implemented with physical knobs, buttons, sliders, dials, selectors or similar on the imaging device or separate from it
- the user interface implemented with digital representations of knobs, buttons, sliders, dials or similar using a display where this display can be either physically attached to the imaging device or connected by wired or wireless means
- a combination of physical and digital user interface described above
- processors P1 and P2 combined into a single processor or their functions distributed over multiple processors,
- some or all of the low-bandwidth sensors being integrated into (a) the imaging device, (b) into a separate unit, or (c) into a display unit,
- some or all of a single set of low-bandwidth sensors being connected to one or several processors that is (are) providing data for use by multiple imaging sensor systems.

Operation of all Sensor Embodiments

The various sensor embodiments described above can be operated in many different modes. In one mode the data gathered from the sensor is analyzed by a processor and used for automatic analysis and decisions (such as triggering of an alarm signal or different operating mode, because a certain limit of gas detection is exceeded) by the processor without being displayed in real-time or near real-time on a display. In another mode an image of the received data can be shown on a display (for example for monitoring by a human operator) however no real-time analysis like gas quantification is performed. In a third mode an image is displayed and automatic gas quantification is performed, and significant results are automatically stored or sent to remote locations. Other combinations and modes of operation are possible as well, for example in conjunction with the use of low-bandwidth sensors like range and weather sensors.

Imaging Turbulent Gas Jets and Absorption Profiles

FIGS. 8A and 8B illustrate two alternative imaging geometries of a potential gas leak, shown as a gas jet exiting a hole in a pressurized pipe and expanding into an ambient atmosphere. Illumination provided by the sun is shown in FIG. 8A to transmit directly through the gas jet and ambient atmosphere towards the SWIR imaging sensor, i.e., the sun is roughly in front of the sensor and the gas leak. In FIG. 8B, artificial illumination comes from near the SWIR imaging sensor behind the gas leak, passes through the gas jet and ambient atmosphere, reflects off background material and heads back to the sensor while passing through the gas jet and ambient atmosphere a second time. A hybrid of these imaging geometries is where the sun is out in front of the sensor beyond the gas leak, but first reflects off the ground then up through the gas towards the sensor. These various imaging geometries differ in three ways; the number of passes through the gas jet (once vs. twice), the optical path length through the ambient atmosphere to be considered ($L_J$ vs. $2L_R$), and change in spectral illumination of the source $S_\lambda$ due to the reflectivity of the background $R_\lambda$. The spectral response of the SWIR sensor will be affected by the solar (or artificial) SWIR illumination, reflectivity of the background, absorption by the gas jet, absorption by the ambient atmosphere, the quantum efficiency of the photo-detector array $Q_\lambda$, and transmission of the filters $F_\lambda$ in combination with the SWIR lens.

The geometry of the gas jet, as shown in FIG. 8, is indicative of a momentum-dominated jet forced from an orifice of effective diameter $D_o$ under pressure. If the internal pipe pressure is approximately twice the external atmospheric pressure, the jet will exhibit critical flow (also termed "choked flow") at the orifice where it just reaches the local speed of sound. The internal pressure and temperature determines the density of the gas at the exit, and hence, the mass-flow of gas out the hole. Beyond the exit hole the gas expands rapidly and adiabatically, and beyond an initial zone of complex acoustic waves, the resulting slip flow of the gas relative to the ambient air goes unstable and transitions to turbulence. This turbulence penetrates across the entire gas jet, entraining air into the jet from the sides, which causes the gas to dilute and the jet to expand in a predictable self-similar flow that is invariant to scale. The gas exiting the hole thus shares its initial momentum with the entrained air, thereby losing initial momentum while buoyancy acts to add momentum in the direction of gravity. In the case of natural gas, the buoyancy force acts upwards as the methane at atmospheric pressure is less dense than air. The heavier hydrocarbons will gain downward momentum due to negative buoyancy. The orientation of the pipe and location of the hole will affect the angle of the jet relative to gravity, and the presence of crosswinds will cause the jet to bend with the wind. The self-similar structure of this turbulent gas jet, its variation along the jet axis and cross-sectional profiles, are well known. For thin cracks, as opposed to approximately round holes, there is also a self-similar solution to the turbulent jet. And at low pressures, where the exit flow is sub-sonic, the jet will rapidly become a buoyant plume that also generates turbulence and exhibits a self-similar structure. Since the variations in jet geometry, gas concentration, and gas density, will all affect the absorption of the SWIR illumination passing through the jet, the absorption imagery of a gas jet can be used from different viewpoints to probe the geometry of the orifice, and determine its approximate shape and size. Combining this information with the internal pressure of the pipe (assumed known from reading a nearby pressure gauge or knowledge of the plumbing network), it is possible to estimate the mass-flow out of the orifice. Thus, the invention provides both imagery of the gas leak and quantification in terms of gas present in the jet and mass-flow out the hole along with estimates of hole shape and size.

FIG. 9A illustrates an absorption image of a methane gas jet exiting a 1 mm diameter round orifice with an internal pressure of 1300 psig (pounds per square inch—psi "gauge", i.e., relative to external atmospheric pressure of approximately 14.5 psi). The absorption image is colored according to a pixel-level differential optical depth scale shown to the right. This corresponds to the degree of absorption in the Core Band relative to the Wings Band for the filters used in the functional prototype of FIG. 3A. This pixel-level differential optical depth is directly proportional to the number of methane molecules along each cone of rays between the light source and the photo-detector corresponding to each pixel; this is the so-called pixel column density of the gas. The turbulent structure of the jet is apparent near the top of the jet image. It is clear from the absorption image that the jet diameter grows linearly along the jet axis, as is consistent with the theoretical self-similar solution for turbulent jets. In this image, it is the noise level of the background differential optical depth that determines the boundary of the jet and so limits the visible diameter.

FIG. 9B shows cross-sectional profiles of the jet absorption image. The graphs plot differential optical depth vs. pixel number across a row of 512 pixels corresponding to the horizontal lines labeled a, b, c in FIG. 9A. It is apparent from these plots that the diameter of these absorption profiles is increasing along the jet axis, and that the turbulence creates fluctuations in absorption through the jet. The general shape of these plots is entirely consistent with the path length through a cross-section of a round jet in combination with a radial concentration profile of Gaussian shape. Superposed on this smooth theoretical profile are fluctuations in concentration due to turbulence.

The maximum of the absorption on each profile should occur on axis of the jet, if the imaging line-of-sight is perpendicular to the jet axis, as this is where the path length through the jet is a maximum and the gas concentration is largest. Based on the self-similar solution for turbulent round jets, the gas concentration on axis will decrease linearly along the jet as it expands, while the diameter increases linearly along the axis, and so the product of axial gas concentration with diameter should remain a constant, suggesting the column density along the jet axis should remain constant. However, due to the turbulent fluctuations, these profiles change over time, and so individual pixel values fluctuate. To cope with these turbulent fluctuations, it is suggested to use spatial averages of quantities across the jet, and then calculate the total absorption of a slice of jet, as it is due to the total mass of gas in that slice and not sensitive to the exact distribution of mass throughout the slice. Each row of pixels along consecutive cross-sections through the jet corresponds to a constant thickness slice, and since the jet diameter varies linearly with axial distance, hence, the slice volume increases as the square of the axial distance. But since the gas concentration dilutes linearly with axial distance in a self-similar round jet, the mass of gas in constant thickness slices is expected to increase linearly with axial distance along the jet. That is, the gas at the front of a jet slice flows slower than the gas at the rear of the jet slice, causing mass to build up between slices of constant thickness. And since the mass of gas in slices increases linearly along the jet axis, so should the absorption due to that mass. Thus, the integrated differential optical depth across each cross-section of the jet image should increase linearly along the jet. Similarly, the jet width in the absorption image should increase linearly along the jet, where the jet boundary is determined by the noise in the background image. Integrating the absorption across jet cross-sections acts to smooth out the effect of turbulent fluctuations on gas concentration in the jet.

FIGS. 10A and 10B plot the automatically extracted jet width and corresponding integrated differential optical depth (integrated-dOD), respectively, along the axial distance (approximately the image row number) for the jet image in FIG. 9A. It is apparent that both quantities follow clear linear trends, and so a least-squares regression line is fit to each quantity. Forming the ratio of integrated differential optical depth to jet width yields an average differential optical depth (average-dOD) value at each axial location along the jet. This ratio is plotted in FIG. 10C, to which a least-squares regression line is fit (starting away from the orifice to exclude the complex acoustic region just outside the hole). It is apparent from FIG. 10C that the slope of this regression line is very small, and that the intercept of the regression line then corresponds to the average differential optical depth extrapolated back to the effective orifice from which the gas leaks under pressure.

FIG. 11 plots the integrated differential optical depth (integrated-dOD) along the axis of a natural gas jet emanating from a narrow (50 micron) slit orifice that is 1 cm long, meant to emulate a crack (instead of a hole) in a pressurized line at 60 psig. Following the same reasoning as above but for a plane turbulent jet (instead of a round turbulent jet), one finds that the integrated-dOD should scale with the square-root of the distance along the axis, as is apparent from the least-squares regression fits in FIG. 11. And since the integrated-dOD across a plane jet is independent of the orientation of the slit relative to the line-of-sight of the sensor, one can use this square-root versus linear behavior to distinguish between a gas leak emanating from a crack or a hole.

Absorption and Mass Flow Across a Range of Pressures and Orifice Sizes

Experiments have been conducted to image the release of methane gas under a range of pressures (50-1400 psig) exiting from round orifices (diameters of 0.75 mm and 1.0 mm). Gas jet boundaries are automatically extracted from the imagery, and the average differential optical depth (Avg-dOD) along the jet axis is computed. Fitting a least-squares regression line to this data determines the intercept of this regression line, which indicates the degree of absorption of the methane at the effective orifice. FIG. 12A plots the value of this Avg-dOD intercept (scaled by orifice diameter) against the internal pressure P (in units of Bar, where 1 Bar=14.5 psi, the atmospheric pressure at sea level). The data points are consistent with a power-law behavior of pressure, for which the scaling constant and exponent values are shown on the graph. This is expected since the absorption by the methane gas at the effective exit hole (extrapolating back from the linear boundaries of the jet) will be proportional to the product of the effective orifice diameter and the local gas density, while the gas density is proportional to a power-law of the pressure through the adiabatic equation of state using the ratio of heat capacities for methane. Further experiments will determine the general utility of this specific power-law relationship across a range of orifice diameters and (approximately round) shapes.

FIG. 12B plots the measured methane mass flow per orifice area (in grams/sec, divided by orifice area) against internal pressure for numerous experiments using round and slot orifices of different sizes. It is clear they follow the expected linear relationship, with a slope determined by the data. The mass flow out of the orifice is proportional to the product of the area of the orifice and the methane gas density in the pipe (which is proportional to the pressure in the pipe). Thus, while the Avg-dOD intercept curve scales linearly with effective diameter of a round orifice (as implied by FIG. 12A), the mass flow scales like the square of the effective diameter of a round orifice (as implied by FIG. 12B). These relationships taken together are therefore used to estimate the orifice size and mass flow of gas directly from the observed absorption image of a gas jet leaking from a hole under known internal pressure. Thus, it is possible to estimate the size of a leak hole directly from a gas jet absorption image, even if the leak hole itself is not visible in the image. And this leads directly to a leak rate or mass flow estimate. Similar relationships apply to a planar gas jet leaking from a narrow crack.

FIG. 13A shows a test setup for imaging and estimating methane mass flow exiting from small round orifices of various sizes at a range of internal pressures up to 1000 psig. Experiments were conducted outdoors in natural sunlight under varying crosswinds. FIG. 13B graphs the data obtained using the setup in FIG. 13A, showing strong correlation between the mass outflows estimated directly from the gas absorption imagery with the measured mass flowing into the gas release manifold, in the presence of crosswinds (Low=0-5 kph, Med=5-10 kph, High >10 kph). This validates the method for estimating gas leak rate from absorption imagery, for holes in pressurized lines.

Next, the mathematical formulation of absorption imaging and quantification of gas leaks is described, using methane or natural gas as a specific example.

Defining the SWIR Spectral Bands

Spectral imagery is taken through at least two filters with transmission exceeding about 5% over wavelength regions that cover the 2350 nm methane feature complex. One filter is narrow (bandwidth approximately 200 nm) and centered at about 2350 nm; call this the Core Filter with transmission $F_C(\lambda)$ and integrated transmission $F_C$. The other filter is broad (bandwidth approximately 400 nm), transmitting between approximately 2100-2500 nm; call this the Surround Filter with transmission $F_S(\lambda)$ and integrated transmission $F_S$.

Remove the overlapping Core Band spectral transmission from the Surround Filter, in order to image the intensity in the spectral Wings Band of methane. Alternatively, use two separate filters that transmit in bands on either side of the Core Band, and combine them into a Wings Band filter. Or use a single broadband filter that spans both sides of the Core Band with a low-transmission notch in the region of the Core Band. It is recommended to use Core Band and Wings Band filters with approximately equal transmission-bandwidth product to balance the dynamic range of the signal in both spectral bands.

Define the core integrated transmission of the Surround Filter as $F_{SC}$ and of the Core Filter as $F_C$, and the imaged intensities in the core and surround pass-bands as $I_C$ and $I_S$, then the intensity in the Wings Band $I_W$ is obtained as $$I_W = I_S - \left[\frac{F_{SC}}{F_C}\right] I_C \quad \text{(Eq. 1)}$$

Calibrating the Sensor in the Ambient Environment

Define the optical depth in the Core Band as $\tau^{(a)}_c$ and the optical depth in the Wings Band as $\tau^{(a)}_w$. Each is the product of the respective absorptivity and path length through the environment (approximating integrals across wavelength bands). Noting the superscript (a) to connote the ambient atmosphere, and using the symbols defined previously and shown in FIG. 8B, the intensities in both bands are given by:

$$I^{(a)}_C = S_C^{(r)} Q_C F_C R_C exp-[\tau^{(a)}_C] \quad \text{(Eq. 2a)}$$

$$I^{(a)}_W = S_W^{(r)} Q_W F_W R_W exp-[\tau^{(a)}_W] \quad \text{(Eq. 2b)}$$

Next form the ratio of these spectral intensities, and note the spectral illumination source function ratio $S_C/S_W$ is independent of distance and only a function of wavelength. Then define the cross-channel Core-to-Wings gain $G_{CW}$ as the ratio of bracketed terms in Eq. 3a, the atmospheric differential absorption coefficient $\delta\alpha^{(a)}$, and path length from sensor to the reflector panel $L_R$. The ratio of Core to Wing intensities is then $$\frac{I_C^{(a)}}{I_W^{(a)}} = \frac{[S_C^{(0)} Q_C F_C R_C]}{[S_W^{(0)} Q_W F_W R_W]} \exp{-[\tau_C^{(a)} - \tau_W^{(a)}]} \qquad \text{(Eq. 3a)}$$

$$\frac{I_C^{(a)}}{I_W^{(a)}} = G_{CW} \exp{-[\alpha_C^{(a)} - \alpha_W^{(a)}]2L_R} = G_{CW} \exp{-[\delta\alpha^{(a)}]2L_R} \qquad \text{(Eq. 3b)}$$

To adaptively calibrate the sensor in the ambient atmosphere, first measure the SWIR illumination bouncing off a reflector panel at two or more distances, calculate the image average intensities, and form the log of their ratio to solve for the unknowns $G_{CW}$ and $\delta\alpha^{(a)}$ (if using more than two distances, solve for the two unknowns via method of least-squares). The resulting value for the gain $G_{CW}$ incorporates the ratio of Core-to-Wings reflectivities of the calibration panel. When the sensor is sufficiently close to the potential leak site, it is not required to account for absorption by the ambient atmosphere, therefore one can forego measurement of reflected light from calibration panels at measured distances, and instead adopt a value of zero distance to such panels. Practical application for methane sensing suggests that distances from 5 to 15 meters are sufficiently close under conditions of a fair atmosphere, however, under foggy conditions, even distances below 5 meters might require the above process to compensate for atmospheric absorption.

Next, rescale the gain $G_{CW}$ using in-scene reflector materials (i.e., background materials). Use a pair of Core and Wings Band images of the in-scene reflector materials (concrete, wood, asphalt, dirt, grass, etc.) together with Eq. 3b to determine an adaptive gain $G_{CW}$ for each reflecting material. It is also possible to generate a library of these gain values for a variety of background materials, and have the user select from a menu the appropriate gain value, or have the sensor system automatically select the appropriate gain value to use while conducting a leak inspection. For direct transmission of sunlight through gas, as in FIG. 8A, the new gain value is obtained by simply imaging in a direction without a background and ignoring atmospheric absorption, using Eq. 3b.

Imaging Possible Gas Leaks (Detection Mode)

To inspect for a possible gas leak, image in the direction of interest. Using the symbols of FIG. 8b for a gas leak of extent (jet width) $D_J$, measure range $L_R$ to the reflecting surface in the background (either the reflector panel or an in-scene reflector). Let $\tau^{(g+a)}$ be the optical depth of the combined gas jet in the ambient environment from the sensor to the reflector at $L_R$ and back to the sensor. Then the intensities in the Core and Wings Bands are Given by $$I^{(g)}_C = S_C^{(r)} Q_C F_C R_C \exp{-[\tau^{(g+a)}_C]} \qquad \text{(Eq. 4a)}$$

$$I^{(g)}_W = S_W^{(r)} Q_W F_W R_W \exp{-[\tau^{(g+a)}_W]} \qquad \text{(Eq. 4b)}$$

Form the ratio of Core to Wings Bands from equations (4), substitute the expression for the cross-channel gain $G_{CW}$ (appropriate for the background surface reflector), define the differential spectral absorption coefficient $\delta\alpha^{(g)}$ of methane or natural gas, and rearrange terms (the superscript "(g)" connotes gas may be present), $$\frac{I_C^{(g)}}{I_W^{(g)}} = G_{CW} \exp{-\{[\delta\alpha^{(g)} - \delta\alpha^{(a)}]2D_J + [\delta\alpha^{(a)}]2L_R\}} \qquad \text{(Eq. 5)}$$

Define the Excess Differential Spectral Absorptivity of the gas jet (diluted methane or natural gas) over that of the ambient atmospheric environment as $$\Delta_{CW}^{g-a} = \delta\alpha^{(g)} - \delta\alpha^{(a)} = [\alpha^{(g)}_C - \alpha^{(g)}_W] - [\alpha^{(a)}_C - \alpha^{(a)}_W] \qquad \text{(Eq. 6)}$$

Therefore, the Differential Optical Depth (dOD) image due to the gas jet is obtained from the measured spectral intensities and calibration parameters via equations (5) and (6) as $$dOD = [\Delta_{CW}^{g-a}]D_J = -\frac{1}{2}\ln\left[\frac{1}{G_{CW}}\frac{I_C^{(g)}}{I_W^{(g)}}\right] - [\delta\alpha^{(a)}]L_R \qquad \text{(Eq. 7a)}$$

In the case of negligible atmospheric absorption as compared to the gas leak (e.g., imaging sufficiently close to a potential leak), the second term on the right can be eliminated by setting $L_R$ to zero, thus $$dOD = -\frac{1}{2}\ln\left[\frac{1}{G_{CW}}\frac{I_C^{(g)}}{I_W^{(g)}}\right] \qquad \text{(Eq. 7b)}$$

The factor of ½ in equation (7b) comes from the double path length through the gas due to reflection of incident light from near or behind the sensor, off the background surface, and back to the sensor. In the case of single pass transmission (e.g., sunlight ahead of the gas leak, passing directly through the gas to the sensor), this factor is simply dropped.

Estimating Jet Mass, Orifice Size, and Methane Mass Flux

From the differential optical depth (dOD) image for a detected jet (or plume or cloud), compute the average-dOD across the jet profiles along its axis, and sum along the axis to obtain the total optical depth of the visible jet according to $$dOD_{jet} = \Sigma_{axis} D_J(z) \overline{dOD}(z) \qquad \text{(Eq. 8)}$$

Relating dOD to the methane molecular column density via the absorption cross-sections $\sigma_C$ and $\sigma_W$ in the Core and Wings Bands (see FIG. 2B), obtain the total number of methane molecules, and multiply by the mass of a methane molecule $m_{CH4}$ to obtain the total mass of methane gas in the visible jet (or plume or cloud) via the expression $$Mass_{CH_4} = \left[\frac{dOD_{jet}}{\sigma_C - \sigma_W}\right] m_{CH_4} \qquad \text{(Eq. 9)}$$

From the differential optical depth (dOD) image for a detected jet, derive the Avg-dOD intercept $\overline{dOD_0}$ by linear regression along the jet axis as explained above and shown in FIG. 10C, and combine with a power-law equation of the form (see FIG. 12A)

$$\overline{dOD_O} = \frac{1}{S} D_O P^k \qquad \text{(Eq. 10a)}$$

Solve for (an approximately round) orifice diameter $D_o$ and substitute for the scale factor and exponent as obtained from the experimental data as shown in FIG. 12A, $$D_O = S\frac{\overline{dOD_0}}{P^k} \cong 110\frac{\overline{dOD_0}}{(P/14.7)^{0.34}} \qquad \text{(Eq. 10b)}$$

Use this orifice diameter $D_o$ to estimate the methane mass flow rate from the orifice flow formula using the linear regression formula shown in FIG. 12B, $$Q_m = \frac{\pi}{4} D_O^2 (0.68P) \cong 0.53 D_O^2 P \qquad (\text{Eq. 11})$$

This mass flow estimate is valid for internal pressures P greater than approximately 1.8 bar (26 psi), such that chocked flow occurs at the leak orifice, with outflow speed at the local sound speed and adiabatic expansion of the gas. The units for the physical quantities in equations (8) through (11) are: optical depth intercept $\overline{dOD_O}$ is dimensionless, diameter $D_0$ in millimeters, pressure P in psig, and methane mass flux $Q_m$ in grams/min.

Surface Emission Mass Flux Under Steady Winds

To estimate surface emission mass flux under conditions of buoyancy and ground-level winds, we consider the imaging geometry shown in FIG. 14A overlooking a ground area upon which gas is detected, similar to the example shown in FIG. 4C. Each emitting surface patch is analyzed using the notation shown in FIG. 14B, and the total surface emission flux is obtained by summing the individual patch emissions.

As illustrated in FIG. 14B, a surface patch by definition is isolated, surrounded by ambient clear air, with winds that are assumed steady in direction and speed V (the case of gusting winds will be considered below). Gas emerges from the ground, diffuses into the air above, and rises (methane) or falls/lingers (for heavier hydrocarbons) due to buoyancy forces. The wind convects the gas downwind as it continues to disperse and rise (as is typically the case for a natural gas leak from an underground pipe). The mass of methane associated with a surface patch is estimated from spectral imaging, which provides the differential spectral optical depth of methane over the entire patch. Summing the pixels over the entire patch, similar to Eq. 8 for the gas jet, and convert to methane mass over the patch as in Eq. 9.

Measure the wind speed V and direction near ground/surface level, and assume it is representative of the wind at the emitting surface patch. Also measure range from the sensor to the surface patch, so that pixel dimensions of the patch can be converted to linear dimensions. The steady wind V (cm/sec) blows methane across the patch and away, as it diffuses out of the ground into the air above the patch, and an equilibrium is established in which the surface emission mass flux $Q_m$ (grams/sec) is balanced by the windblown mass crossing the downwind boundary of the patch. The methane layer above the surface patch has a characteristic thickness D and concentration c which give rise to the measured differential optical depth dOD at each pixel. By adjusting the threshold on the optical depth to a low level above the noise floor, the spatial extent of an emitting patch is defined. Construct the bounding rectangle around that patch such that one axis of the rectangle aligns with the wind direction, as illustrated in FIG. 14B. Using the range measured to the patch, convert pixel dimensions of this bounding rectangle to linear dimensions L and W. The volume flux (cm³/sec) across the downwind boundary of the patch is equivalent to the volume flux DWV across side W of the rectangle. The methane mass flux $Q_m$ (grams/sec) is obtained from the product of the methane concentration in air, methane density, and volume flux across the downwind boundary;

$$Q_m = c\rho_{CH_4} DWV \qquad (\text{Eq. 12a})$$

Expressing $c\rho_{CH_4}D$ in terms of the differential spectral optical depth dOD, obtain the estimate of methane mass flux from a patch in steady wind:

$$Q_m = \left[\frac{m}{\sigma_B - \sigma_{ref}}\right]_{CH_4} WV(dOD) \qquad (\text{Eq. 12b})$$

As the imaging geometry shown in FIG. 14A suggests possible oblique sensing, at an angle of $\phi$ relative to the vertical, through the gas layer above the ground surface, the measured differential optical depth should be scaled by cosine ($\phi$) so as to relate to the physical thickness of the layer as denoted by D. The same oblique imaging geometry results in a foreshortening of the ground surface in the down-range direction in the imagery. One can correct the measured optical depth and surface patch dimensions by projecting all sensor data and imagery to the ground plane using the known tilt of the sensor relative to the ground plane (as is commonly done when ortho-rectifying imagery), as if viewing the surface patch from directly above.

Surface Emission Mass Flux Under Gusting Winds

Similar to the formulation for steady winds, gas diffuses out of the ground into the air above the surface patch and builds up a gas layer as the wind blows it away. However, when a gust occurs, the wind rapidly blows the entire layer of methane away. In gusting winds, the methane layer alternates between building itself up (in steady winds of speed V) and being rapidly destroyed by a sudden gust. This allows the build-up of a methane layer to be observed over time. The build-up of methane mass above the patch is the surface emission mass flux $Q_m$ minus the mass flux due to steady wind V as in Eq.12B, $$\frac{dM_{CH_4}}{dt} = Q_m - \left[\frac{m}{\sigma_B - \sigma_{ref}}\right]_{CH_4} WV(dOD) \qquad (\text{Eq. 13a})$$

However, direct observation of the accumulation of methane is possible by imaging the time-varying differential optical depth over the patch, since $$\left.\frac{dM_{CH_4}}{dt}\right]_{obs} = A_P \rho_{CH_4} \frac{d}{dt}(cD) = \left[\frac{m}{\sigma_B - \sigma_{ref}}\right]_{CH_4} A_P \frac{d}{dt}(dOD) \qquad (\text{Eq. 13b})$$

Here $A_p$ is the area of the patch observed before the gust, D is the changing thickness of the methane layer above the patch, and c is the increasing concentration of methane as the layer grows until the next gust. Equating expressions Eq. 13a and Eq. 13b, we obtain an estimate of the methane mass flux $Q_m$ (grams/time) from a surface patch in gusting wind by observing the time-varying differential optical depth as the methane layer is reestablished under steady wind conditions;

$$Q_m = \left[\frac{m}{\sigma_B - \sigma_{ref}}\right]_{CH_4} \left\{A_P \frac{d}{dt}(dOD) + WV(dOD)\right\} \qquad (\text{Eq. 13c})$$

CONCLUSION, RAMIFICATIONS AND SCOPE

The embodiments as described above consist of both multispectral SWIR sensors for imaging, detecting and localizing methane and other hydrocarbon gases, and methods to estimate the leak rate or mass flux. Multiple embodiments of sensor systems have been described to enable imaging of gas leaks, and multiple methods have been disclosed for estimating methane mass flux from holes in pressurized lines, and from surface patch emissions due to underground gas pipe leaks. Example imagery and leak rate estimates across a wide variety of conditions illustrate the viability of the sensors and methods.

Summarizing the advantages of the invention over existing alternative gas imaging technologies, we note the ability to image and quantify gas leaks using natural sunlight without the need for any thermal contrast between the gas and the background, the ability to image and quantify methane in the presence of water vapor and fog, and the ability to quantify leak rates and surface emission flux in order to assess leak severity and prioritize repairs. These capabilities have application in gas safety, gas leak inspection, and greenhouse gas emissions monitoring.

While the above description contains much specificity, these should not be construed as limitations on the scope, but rather as exemplification of several embodiments thereof. Many other variations are possible. For example, by selecting the appropriate spectral filters in the SWIR, the invention can be used for detecting and quantifying other gases, liquids, emulsions, powders, and solids, in addition to the ones cited above and discussed in detail. Thus, multiple spectral filters can be selected to detect ammonia gas, which is both combustible and toxic. Also fertilizers can be detected and quantified, as can soil wetness and general plant health, thus other embodiments may be well suited for agricultural assessments. Yet other embodiments can be constructed that are well suited for detection of ammonium nitrate and its variants as used in the making of homemade explosives. Additionally, the methods developed for leak rate quantification of gases can be utilized for detecting gases and other substances in other spectral bands, in addition to the SWIR band. Accordingly, the scope should be determined not by the embodiments illustrated, but by the appended claims and legal equivalents.

What is claimed is:

1. A method for characterizing mass flow of a hydrocarbon gas jet comprising a hydrocarbon compound of interest leaking from a leak hole in an object, the method comprising:
   a. receiving, by a processor, calibrated differential optical depth (dOD) image of said hydrocarbon gas jet leaking from said object, the calibrated dOD image having been generated via an imaging device and using multispectral images representing intensities of distinguishably detected light of wavelengths within two or more spectral bands, wherein at least a first one of said spectral bands is spanned by one or more spectral feature(s) of said hydrocarbon compound of interest, and at least a second one of said spectral bands is different from the first spectral band; and
   b. determining, by the processor, using the calibrated dOD image in combination with a value of an internal pressure of the object, at least one quantity selected from the group consisting of a total absorption of the hydrocarbon compound of interest, a total mass of the hydrocarbon compound of interest, a diameter of an approximately round hole from which the hydrocarbon compound of interest leaks, and a mass flow rate of the hydrocarbon compound of interest out of the object.

2. The method of claim 1, wherein the calibrated dOD image comprises a plurality of pixels, each having a value representing a pixel level differential optical depth (dOD) and providing a measure of absorption of light by the hydrocarbon compound of interest as the light travels from a particular location within a field of regard to the imaging device.

3. The method of claim 1, comprising estimating, by the processor, the mass flow rate of said hydrocarbon compound of interest out of the leak hole by:
   detecting, within the dOD image, a jet of the hydrocarbon compound of interest originating from the leak hole;
   determining, for each of a plurality of axial locations along the detected jet, a corresponding average differential optical depth across a cross sectional profile of the detected jet, thereby obtaining a plurality of average differential optical depth data points;
   determining, based on the plurality of average differential optical depth data points, an average differential optical depth intercept value corresponding to an axial location at a vertex of the jet that is associated with the leak hole;
   determining, based on the average optical depth intercept value and the value of internal pressure of the object from which said hydrocarbon compound of interest leaks, a size of the leak hole; and
   determining the mass flow rate of said hydrocarbon compound of interest out of the leak hole based on the determined leak hole size and the value of internal pressure of the object from which the hydrocarbon compound of interest leaks.

4. The method of claim 1, wherein the imaging device by which the calibrated dOD image was generated comprises:
   one or more photo-detectors appreciably responsive to light in a wavelength range of approximately 1.0 to 2.6 microns, and positioned to detect light from a plurality of locations within a desired field-of regard;
   at least two spectral filters associated with said one or more photo-detectors, wherein:
      a first spectral filter of the at least two spectral filters is appreciably transmissive to light of wavelengths within the first spectral band spanned by the one or more spectral feature(s) of the hydrocarbon compound of interest, and
      a second spectral filter of the at least two spectral filters-is appreciably transmissive to light of wavelengths within the second spectral band, and
   one or more optical elements aligned and operable to gather and focus incident illumination through the at least two spectral filters, and onto the one or more photo-detectors, thereby providing for generation of multispectral images representing intensities of the detected light of wavelengths within at least the first and second spectral bands, respectively; and
   the processor, wherein the processor is operable to:
      receive the multispectral images; and
      generate, the calibrated dOD images using (i) the received multispectral images in combination with (ii) at least one cross channel gain representing a relative gain between at least the first and the second spectral bands.

5. The method of claim 1, wherein the first spectral band is spanned by a plurality of spectral features of the hydrocarbon compound of interest.

6. The method of claim 1, wherein the first spectral band ranges from about 2.1 to about 2.6 microns.

7. The method of claim 1, wherein the first spectral band has a bandwidth of about 100 nm or more.

8. The method of claim 1, wherein the second spectral band is not spanned by the one or more spectral feature(s) of the hydrocarbon compound of interest.

9. An imaging system for detection of hydrocarbon compounds, the system comprising:
   (a) one or more photo-detectors appreciably responsive to light in a wavelength range of approximately 1.0 to 2.6 microns, and positioned to detect light from a plurality of locations within a desired field-of-regard;
   (b) two or more spectral filters associated with the one or more photo-detectors, wherein:
      a first spectral filter of the two or more spectral filters (i) is appreciably transmissive to light of wavelengths within a first spectral band spanned by one or more spectral feature(s) of a hydrocarbon compound of interest and (ii) is positioned in front of a first portion of the one or more photo-detectors, such that at least a portion of the detected light passes through the first spectral filter before striking the first portion of the one or more photo-detectors; and
      a second spectral filter of the two or more spectral filters (i) is appreciably transmissive to light of wavelengths within a second spectral band that is different from the first spectral band and (ii) is positioned in front of a second portion of the one or more photo-detectors, such that at least a portion of the detected light passes through the second spectral filter before striking the second portion of the one or more photo-detectors,
      thereby providing for distinguishable detection of light of wavelengths within at least the first and second spectral bands;
   (c) one or more optical elements aligned and operable to gather and focus incident illumination from the light source through the two or more spectral filters and onto the one or more photo-detectors, thereby providing for generation of multispectral images representing intensities of the detected light of wavelengths within at least the first and second spectral bands, respectively; and
   (d) a processor operable to:
      receive the multispectral images;
      generate, using (i) the received multispectral images, in combination with, (ii) at least one cross channel gain representing a relative gain between at least the first and second spectral bands, a calibrated differential optical depth (dOD) image; and
      use the differential optical depth absorption image in combination with a value of internal pressure of an object from which the hydrocarbon compound of interest leaks-to estimate at least one quantity selected from the group consisting of: a total absorption of the hydrocarbon compound of interest, a total mass of the hydrocarbon compound of interest, a diameter of an approximately round hole from which the hydrocarbon compound of interest leaks, and a mass flow rate of the hydrocarbon compound of interest out of the object.

10. The imaging system of claim 9, wherein the calibrated dOD image comprises a plurality of pixels, each having a value representing a pixel-level differential optical depth (dOD) and providing a measure of absorption of light, by the hydrocarbon compound of interest, as the light travels along a particular cone of rays from a particular location within the field of regard and to the one or more photo-detectors.

11. The imaging system of claim 10, wherein for at least a portion of the pixels, the value representing the pixel-level dOD is substantially proportional to a number of molecules of the hydrocarbon compound of interest along the particular cone of rays.

12. The imaging system of claim 9, wherein the processor is operable to compute the at least one cross channel gain based on multispectral images obtained via detection of light having wavelengths within at least the first and second spectral bands and having been reflected by a reflective calibration target.

13. The imaging system of claim 12, wherein the processor is operable to:
   computing a differential atmospheric absorption coefficient based on (i) the multispectral images obtained via detection of light having wavelengths within at least the first and second spectral bands and having been reflected by a reflective calibration target and (ii) a value representative of a distance to the reflective calibration target; and
   generate the calibrated dOD image using the computed differential atmospheric absorption coefficient, thereby to calibrating the dOD image for atmospheric absorption.

14. The imaging system of claim 9, wherein the processor is operable to rescale the at least one cross channel gain coefficient to adapt to reflectivities of in-scene reflectors and use the at least one rescaled cross channel gain coefficient to generate the calibrated dOD image.

15. The imaging system of claim 9, wherein the processor is operable to estimate the mass flow rate of the hydrocarbon compound of interest out of the leak hole by:
   detecting, within the dOD image, a jet of the hydrocarbon compound of interest originating from the leak hole;
   determining, for each of a plurality of axial locations along the detected jet, a corresponding average differential optical depth across a cross sectional profile of the detected jet, thereby obtaining a plurality of average differential optical depth data points;
   determining, based on the plurality of average differential optical depth data points, an average differential optical depth intercept value corresponding to an axial location at a vertex of the jet that is associated with the leak hole;
   determining, based on the average optical depth intercept value and the value of internal pressure of the object from which said hydrocarbon compound of interest leaks, a size of the leak hole; and
   determining the mass flow rate of said hydrocarbon compound of interest out of the leak hole based on the determined leak hole size and the value of internal pressure of the object from which the hydrocarbon compound of interest leaks.

16. The imaging system of claim 9, wherein the differential optical depth absorption image comprises a representation of emission from a ground surface patch and wherein the processor is operable to receive use the dOD image in combination with a value of near ground-level wind speed and direction to estimate a surface emission mass flux of said hydrocarbon of interest.

17. The imaging system of claim 9, further comprising-a visible light camera aligned to have approximately parallel lines-of-sight and a field-of-view overlapping with the field-of-regard imaged by the one or more detectors, and wherein the processor is operable to overlay the dOD absorption image of the hydrocarbon compound of interest on a visible light image obtained with the visible light camera, thereby providing spatial context.

18. The imaging system of claim 9, wherein the one or more photo-detectors comprise one or more two-dimensional photo-detector array(s).

19. The imaging system of claim 9, wherein the one or more photo-detectors comprise one or more one-dimensional photo-detector array(s).

20. The imaging system of claim 9, comprising an opto-mechanical scanning device operable to scan a field-of-view of the one or more one-dimensional photo-detector array(s) along a direction substantially perpendicular relative to an orientation of the one-dimensional photo-detector array(s).

21. The imaging system of claim 9, comprising one or more discrete photo-detectors.

22. The imaging system of claim 21, comprising an opto-mechanical scanning device operable to scan in two substantially perpendicular directions, thereby establishing the desired field-of-regard imaged by the one or more discrete photo-detectors.

23. The imaging system of claim 9, wherein the hydrocarbon compound of interest is a gas selected from the group consisting of methane, ethane, propane, butane, pentane, hexane, and octane.

24. The system of claim 9, wherein the first spectral band is spanned by a plurality of spectral features of the hydrocarbon compound of interest.

25. The system of claim 9, wherein the first spectral band ranges from about 2.1 to about 2.6 microns.

26. The system of claim 9, wherein the first spectral band has a bandwidth of about 100 nm or more.

27. The system of claim 9, wherein the second spectral band is not spanned by the one or more spectral feature(s) of the hydrocarbon compound of interest.

* * * * *